United States Patent
Villar De Andrade E Silva et al.

(10) Patent No.: US 11,346,833 B2
(45) Date of Patent: May 31, 2022

(54) RESERVOIR FLUID CHARACTERIZATION SYSTEM

(71) Applicant: Schlumberger Technology Corporation, Sugar Land, TX (US)

(72) Inventors: Vitor Villar De Andrade E Silva, Houston, TX (US); John Rasmus, Richmond, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 389 days.

(21) Appl. No.: 16/250,307

(22) Filed: Jan. 17, 2019

(65) Prior Publication Data
US 2019/0219558 A1 Jul. 18, 2019

Related U.S. Application Data

(60) Provisional application No. 62/618,170, filed on Jan. 17, 2018.

(51) Int. Cl.
*G01N 33/28* (2006.01)
*E21B 43/34* (2006.01)
*G01V 5/00* (2006.01)

(52) U.S. Cl.
CPC ......... *G01N 33/2823* (2013.01); *E21B 43/34* (2013.01); *G01V 5/00* (2013.01)

(58) Field of Classification Search
CPC ....... G01N 33/2823; E21B 43/34; G01V 5/00
USPC .......................................................... 702/24
See application file for complete search history.

(56) References Cited

U.S. PATENT DOCUMENTS

| 6,318,146 B1 * | 11/2001 | Madsen | A61B 8/08 |
| | | | 324/308 |
| 2004/0104048 A1 * | 6/2004 | Woodburn | G01V 3/32 |
| | | | 175/50 |
| 2005/0272158 A1 * | 12/2005 | Galford | G01N 24/081 |
| | | | 436/29 |
| 2007/0119244 A1 * | 5/2007 | Goodwin | G01N 33/2823 |
| | | | 73/152.28 |
| 2010/0057409 A1 | 3/2010 | Jones et al. | |
| 2010/0271019 A1 * | 10/2010 | Anand | G01R 33/305 |
| | | | 324/303 |

(Continued)

FOREIGN PATENT DOCUMENTS

| WO | 2005065277 A2 | 7/2005 |
| WO | 2017074884 A1 | 5/2017 |

OTHER PUBLICATIONS

Soyer et al., "RLM-3D Multiphysics Inversion Modeling: De-Risking Resource Concept Models", Feb. 2020. (Year: 2020).*

(Continued)

*Primary Examiner* — Michael P Nghiem
(74) *Attorney, Agent, or Firm* — Jeffrey D. Frantz

(57) ABSTRACT

A method can include receiving measurements of a fluid mixture where the measurements are acquired by at least one downhole tool; performing a multiphysics inversion of the measurements to generate nuclear parameter values for the fluid mixture; performing a multivariate interpolation using the generated nuclear parameter values that accounts for intermolecular interactions in the fluid mixture; and determining a composition of the fluid mixture based on the multivariate interpolation.

17 Claims, 19 Drawing Sheets

(56) References Cited

U.S. PATENT DOCUMENTS

| | | | | |
|---|---|---|---|---|
| 2012/0053838 A1* | 3/2012 | Andrews | ............... | E21B 49/082 |
| | | | | 702/8 |
| 2013/0311096 A1* | 11/2013 | Greer | ................... | E21B 49/005 |
| | | | | 702/9 |
| 2017/0364149 A1* | 12/2017 | Lu | ........................... | G06F 3/013 |
| 2018/0058211 A1* | 3/2018 | Liang | ..................... | G01V 1/282 |
| 2019/0129056 A1 | 5/2019 | Rasmus et al. | | |

OTHER PUBLICATIONS

Olver, "On Multivariate Interpolation", Apr. 2016. (Year: 2016).*
Silva et al., "Novel Estimation of Reservoir Fluid Composition Using Nuclear Measurements", Abstract, Jun. 2, 2018. (Year: 2018).*
Danesh, A., "Phase Behavior Calculations", In PVT and Phase Behavior of Petroleum Reservoir Fluids, Elsevier Developments in Petroleum Science 47, 1998, pp. 167-207.
Griffiths, R. et al., "Formation Evaluation in High Angle and Horizontal Wells—A New and Practical Workflow", Paper FF presented at the SPWLA 53rd Annual Logging Symposium, Jun. 2012, 16 pages.
McKeon, D. et al., "SNUPAR—A Nuclear Parameter Code for Nuclear Geophysical Applications", IEEE Transactions an Nuclear Science, 1989, v. 36(1), pp. 1215-1219.
Péneloux, A., et al., "A Consistent Correction for Redlich-Kwong-Soave Volumes", Fluid Phase Equilibria, 1982, 8 (1), pp. 7-23.
Peng, D.-Y. et al., "A New Two-Constant Equation of State", Industrial & Engineering Chemistry Fundamentals, 1976, 15(1), pp. 59-64.
Ramdharee, S. et al., "A Review of the Equations of State and their Applicability in Phase Equilibrium Modeling", International Conference on Chemical and Environmental Engineering, Apr. 2013, Johannesburg, South Africa, pp. 84-87.
Soave, G., "Equilibrium constants from a modified Redlich-Kwong equation of state", Chemical Engineering Science, 1972, 27(6), pp. 1197-1203.
Valdisturlo, A. et al., "Improved Petrophysical Analysis in Horizontal Wells: From Log Modeling Through Formation Evaluation to Reducing Model Uncertainty—A Case Study", Paper SPE-16881-MS, presented at the EAGE Annual Conference & Exhibition incorporating SPE Europec, Jun. 2013, 13 pages.
Whitson, C.H. et al., "Equation-of-State Calculations", in C. H. Whitson, & M. R. Brulé, Phase Behavior, 2000, 20, Richardson, Texas, SPE Monograph Series, pp. 47-55.
Xie, H. et al., "Workflow for Determining Layer Properties from Density and Neutron Logs in High-Angle and Horizontal Wells", Paper 182964-MS presented at the Abu Dhabi International Petroleum Exhibition & Conference, Nov. 2016, 14 pages.

* cited by examiner

GUI System 400

GUI 405

GUI 410

Compostional Plot at Depth 430

RESERVOIR FLUID CHARACTERIZATION SYSTEM

RELATED APPLICATIONS

This application claims priority to and the benefit of a U.S. Provisional Application having Ser. No. 62/618,170, filed 17 Jan. 2018, which is incorporated by reference herein.

BACKGROUND

Rock can be formed of an aggregate of material. For example, rock may be formed of one or more of minerals, organic matter, volcanic glass, etc. Rock may include a single type of mineral or many types of minerals. Rocks may be characterized by types such as, for example, sedimentary rocks like sandstone and limestone (e.g., formed at the Earth's surface through deposition of sediments derived from weathered rocks, biogenic activity or precipitation from solution); igneous rocks (e.g., originating deeper within the Earth, where the temperature may be high enough to melt rocks, to form magma that can crystallize within the Earth or lava at the surface by volcanic activity); and metamorphic rocks (e.g., formed from other preexisting rocks during episodes of deformation of the Earth at temperatures and pressures high enough to alter minerals but inadequate to completely melt them). Changes to rock may occur by the activity of fluids in the Earth's movement of igneous bodies or regional tectonic activity. A reservoir can be a porous permeable rock formation, which may be detrital. A reservoir may be rocks that include one or more types of fluid (e.g., water, oil, hydrocarbon gas, etc.). Rocks may be recycled from one type to another by the constant changes in the Earth. As such, rocks may be considered to have associated "histories", which can add a temporal aspect to rocks found today.

SUMMARY

A method can include receiving measurements of a fluid mixture where the measurements are acquired by at least one downhole tool; performing a multiphysics inversion of the measurements to generate nuclear parameter values for the fluid mixture; performing a multivariate interpolation using the generated nuclear parameter values that accounts for intermolecular interactions in the fluid mixture; and determining a composition of the fluid mixture based on the multivariate interpolation. A system can include a processor; memory accessibly by the processor; and instructions stored in the memory and executable by the processor to instruct the system to: receive measurements of a fluid mixture where the measurements are acquired by at least one downhole tool; perform a multiphysics inversion of the measurements to generate nuclear parameter values for the fluid mixture; perform a multivariate interpolation using the generated nuclear parameter values that accounts for intermolecular interactions in the fluid mixture; and determine a composition of the fluid mixture based on the multivariate interpolation. One or more computer-readable storage media can include processor-executable instructions where the processor-executable instructions include instructions to instruct a computer to: receive measurements of a fluid mixture where the measurements are acquired by at least one downhole tool; perform a multiphysics inversion of the measurements to generate nuclear parameter values for the fluid mixture; perform a multivariate interpolation using the generated nuclear parameter values that accounts for intermolecular interactions in the fluid mixture; and determine a composition of the fluid mixture based on the multivariate interpolation. Various other apparatuses, systems, methods, etc., are also disclosed.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

Features and advantages of the described implementations can be more readily understood by reference to the following description taken in conjunction with the accompanying drawings.

DETAILED DESCRIPTION

This description is not to be taken in a limiting sense, but rather is made merely for the purpose of describing the general principles of the implementations. The scope of the described implementations should be ascertained with reference to the issued claims.

Figure 1:
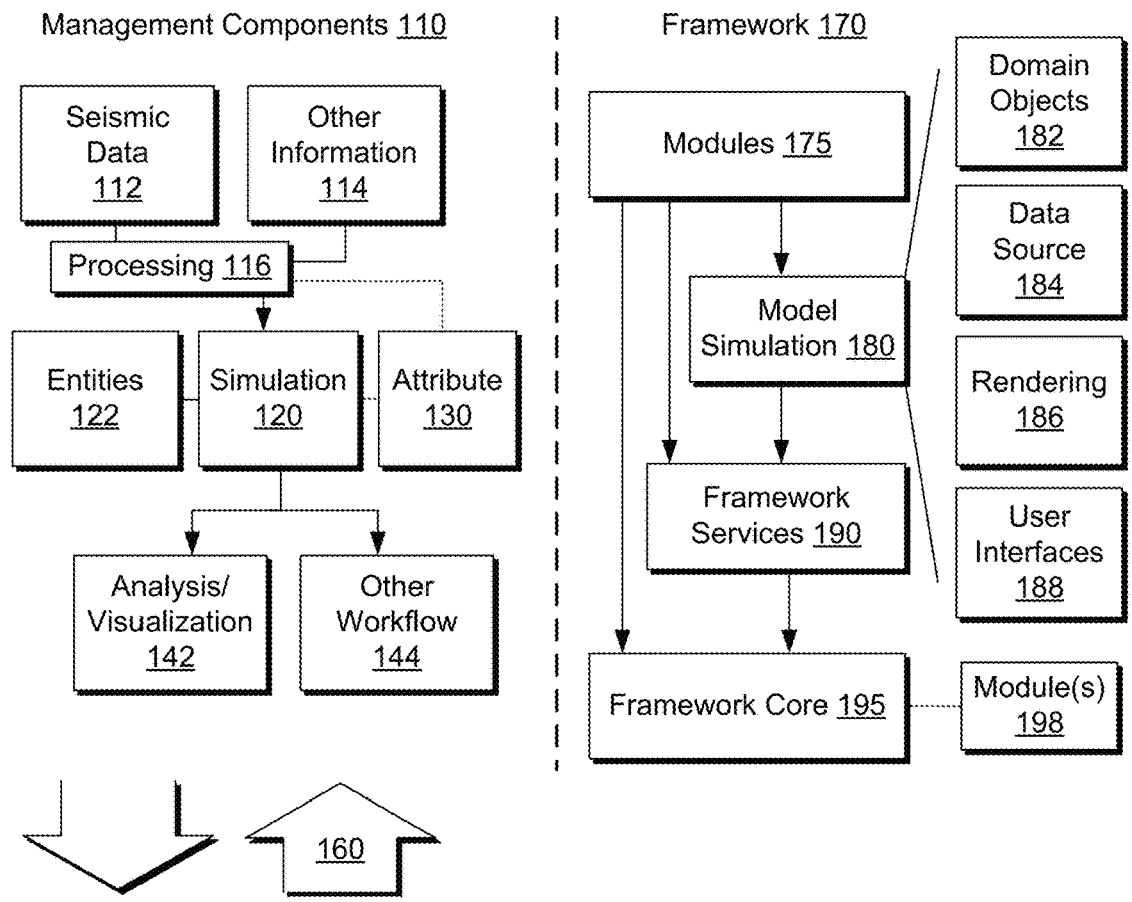
FIG. 1 illustrates an example system that includes various components for simulating a geological environment.
Figure 1:
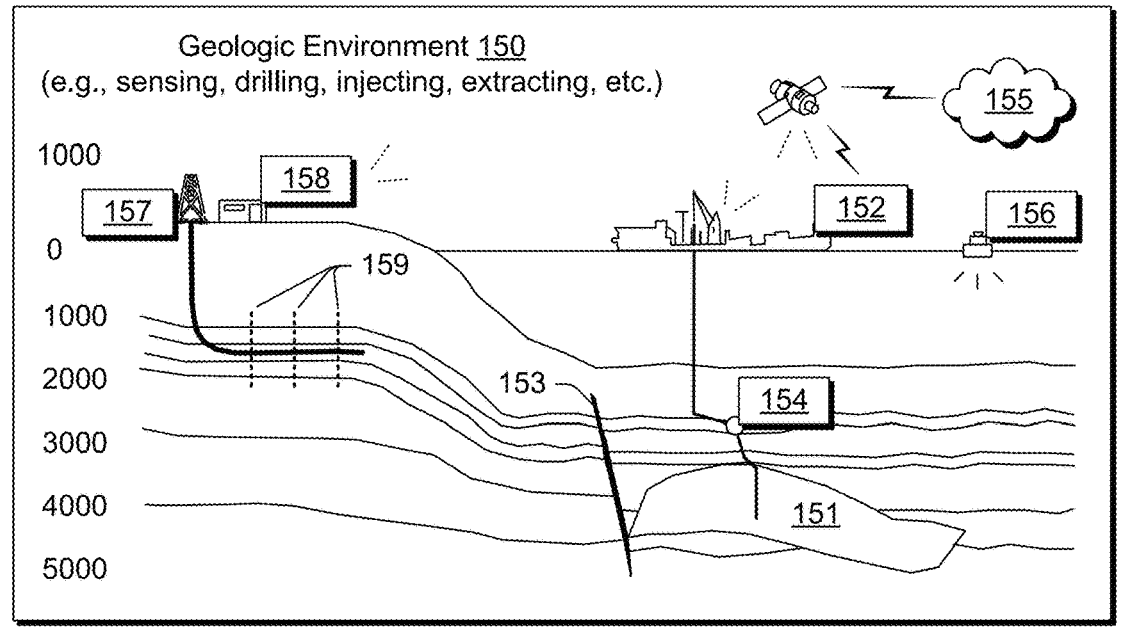

FIG. 1 shows an example of a system 100 that includes various management components 110 to manage various aspects of a geologic environment 150 (e.g., an environment that includes a sedimentary basin, a reservoir 151, one or more fractures 153, etc.). For example, the management components 110 may allow for direct or indirect management of sensing, drilling, injecting, extracting, etc., with respect to the geologic environment 150. In turn, further information about the geologic environment 150 may become available as feedback 160 (e.g., optionally as input to one or more of the management components 110).

In the example of FIG. 1, the management components 110 include a seismic data component 112, an additional information component 114 (e.g., well/logging data), a processing component 116, a simulation component 120, an attribute component 130, an analysis/visualization component 142 and a workflow component 144. In operation, seismic data and other information provided per the components 112 and 114 may be input to the simulation component 120.

In an example embodiment, the simulation component 120 may rely on entities 122. Entities 122 may include earth entities or geological objects such as wells, surfaces, reservoirs, etc. In the system 100, the entities 122 can include virtual representations of actual physical entities that are reconstructed for purposes of simulation. The entities 122 may include entities based on data acquired via sensing, observation, etc. (e.g., the seismic data 112 and other information 114). An entity may be characterized by one or more properties (e.g., a geometrical pillar grid entity of an earth model may be characterized by a porosity property). Such properties may represent one or more measurements (e.g., acquired data), calculations, etc.

In an example embodiment, the simulation component 120 may operate in conjunction with a software framework such as an object-based framework. In such a framework, entities may include entities based on pre-defined classes to facilitate modeling and simulation. An example of an object-based framework is the MICROSOFT .NET framework (Redmond, Wash.), which provides a set of extensible object classes. In the .NET framework, an object class encapsulates a module of reusable code and associated data structures. Object classes can be used to instantiate object instances for use by a program, script, etc. For example, borehole classes may define objects for representing boreholes based on well data. A model of a basin, a reservoir, etc. may include one or more boreholes where a borehole may be, for example, for measurements, injection, production, etc. As an example, a borehole may be a wellbore of a well, which may be a completed well (e.g., for production of a resource from a reservoir, for injection of material, etc.).

In the example of FIG. 1, the simulation component 120 may process information to conform to one or more attributes specified by the attribute component 130, which may include a library of attributes. Such processing may occur prior to input to the simulation component 120 (e.g., consider the processing component 116). As an example, the simulation component 120 may perform operations on input information based on one or more attributes specified by the attribute component 130. In an example embodiment, the simulation component 120 may construct one or more models of the geologic environment 150, which may be relied on to simulate behavior of the geologic environment 150 (e.g., responsive to one or more acts, whether natural or artificial). In the example of FIG. 1, the analysis/visualization component 142 may allow for interaction with a model or model-based results (e.g., simulation results, etc.). As an example, output from the simulation component 120 may be input to one or more other workflows, as indicated by a workflow component 144.

As an example, the simulation component 120 may include one or more features of a simulator such as the ECLIPSE reservoir simulator (Schlumberger Limited, Houston, Tex.), the INTERSECT reservoir simulator (Schlumberger Limited, Houston, Tex.), the VISAGE geomechanics simulator (Schlumberger Limited, Houston, Tex.), the PETROMOD petroleum systems simulator (Schlumberger Limited, Houston, Tex.), the PIPESIM network simulator (Schlumberger Limited, Houston, Tex.), TECHLOG petrophysical framework (Schlumberger Limited, Houston, Tex.), etc. The ECLIPSE simulator includes numerical solvers that may provide simulation results such as, for example, results that may predict dynamic behavior for one or more types of reservoirs, that may assist with one or more development schemes, which may assist with one or more production schemes, etc. The VISAGE simulator includes finite element numerical solvers that may provide simulation results such as, for example, results as to compaction and subsidence of a geologic environment, well and completion integrity in a geologic environment, cap-rock and fault-seal integrity in a geologic environment, fracture behavior in a geologic environment, thermal recovery in a geologic environment, $CO_2$ disposal, etc. The PETROMOD simulator includes finite element numerical solvers that may provide simulations results such as, for example, results as to structural evolution, temperature, and pressure history and as to effects of such factors on generation, migration, accumulation, and loss of oil and gas in a petroleum system through geologic time. Such a simulator can provide properties such as, for example, gas/oil ratios (GOR) and API gravities, which may be analyzed, understood, and predicted as to a geologic environment. The PIPESIM simulator includes solvers that may provide simulation results such as, for example, multiphase flow results (e.g., from a reservoir to a wellhead and beyond, etc.), flowline and surface facility performance, etc. The PIPESIM simulator may be integrated, for example, with the AVOCET production operations framework (Schlumberger Limited, Houston Tex.). As an example, a reservoir or reservoirs may be simulated with respect to one or more enhanced recovery techniques (e.g., consider a thermal process such as SAGD, etc.).

In an example embodiment, the management components 110 may include features of a framework such as the PETREL seismic to simulation software framework (Schlumberger Limited, Houston, Tex.). The PETREL framework provides components that allow for optimization of exploration and development operations. The PETREL framework includes seismic to simulation software components that can output information for use in increasing reservoir performance, for example, by improving asset team productivity. Through use of such a framework, various professionals (e.g., geophysicists, geologists, and reservoir engineers) can develop collaborative workflows and integrate operations to streamline processes (e.g., with respect to one or more geologic environments, etc.). Such a framework may be considered an application (e.g., executable using one or more devices) and may be considered a data-driven application (e.g., where data is input for purposes of modeling, simulating, etc.).

In an example embodiment, various aspects of the management components 110 may include add-ons or plug-ins that operate according to specifications of a framework environment. For example, a framework environment marketed as the OCEAN framework environment (Schlumberger Limited, Houston, Tex.) allows for integration of add-ons (or plug-ins) into a PETREL framework workflow. The OCEAN framework environment leverages .NET tools (Microsoft Corporation, Redmond, Wash.) and offers stable, user-friendly interfaces for efficient development. In an example embodiment, various components may be implemented as add-ons (or plug-ins) that conform to and operate according to specifications of a framework environment (e.g., according to application programming interface (API) specifications, etc.).

FIG. 1 also shows an example of a framework 170 that includes a model simulation layer 180 along with a framework services layer 190, a framework core layer 195 and a modules layer 175. The framework 170 may include the OCEAN framework where the model simulation layer 180 is the PETREL model-centric software package that hosts OCEAN framework applications. In an example embodiment, the PETREL software may be considered a data-driven application. The PETREL software can include a framework for model building and visualization. Such a model may include one or more grids.

The model simulation layer 180 may provide domain objects 182, act as a data source 184, provide for rendering 186 and provide for various user interfaces 188. Rendering 186 may provide a graphical environment in which applications can display their data while the user interfaces 188 may provide a common look and feel for application user interface components.

In the example of FIG. 1, the domain objects 182 can include entity objects, property objects and optionally other objects. Entity objects may be used to geometrically represent wells, logs, core data, surfaces, reservoirs, etc., while property objects may be used to provide property values as well as data versions and display parameters. For example, an entity object may represent a well where a property object provides log information as well as version information and display information (e.g., to display the well as part of a model).

In the example of FIG. 1, data may be stored in one or more data sources (or data stores, generally physical data storage devices), which may be at the same or different physical sites and accessible via one or more networks. The model simulation layer 180 may be configured to model projects. As such, a particular project may be stored where stored project information may include inputs, models, results and cases. Thus, upon completion of a modeling session, a user may store a project. At a later time, the project can be accessed and restored using the model simulation layer 180, which can recreate instances of the relevant domain objects.

In the example of FIG. 1, the geologic environment 150 may include layers (e.g., stratification) that include a reservoir 151 and that may be intersected by a fault 153. As an example, the geologic environment 150 may be outfitted with any of a variety of sensors, detectors, actuators, etc. For example, equipment 152 may include communication circuitry to receive and to transmit information with respect to one or more networks 155. Such information may include information associated with downhole equipment 154, which may be equipment to acquire information, to assist with resource recovery, etc. Other equipment 156 may be located remote from a well site and include sensing, detecting, emitting or other circuitry. Such equipment may include storage and communication circuitry to store and to communicate data, instructions, etc. As an example, one or more satellites may be provided for purposes of communications, data acquisition, etc. For example, FIG. 1 shows a satellite in communication with the network 155 that may be configured for communications, noting that the satellite may additionally or alternatively include circuitry for imagery (e.g., spatial, spectral, temporal, radiometric, etc.).

FIG. 1 also shows the geologic environment 150 as optionally including equipment 157 and 158 associated with a well that includes a substantially horizontal portion that may intersect with one or more formation layers and/or one or more fractures 159. For example, consider a well in a shale formation that may include natural fractures, artificial fractures (e.g., hydraulic fractures) or a combination of natural and artificial fractures. As an example, a well may be drilled for a reservoir that is laterally extensive. In such an example, lateral variations in properties, stresses, etc. may exist where an assessment of such variations may assist with planning, operations, etc. to develop a laterally extensive reservoir (e.g., via fracturing, injecting, extracting, etc.). As an example, the equipment 157 and/or 158 may include components, a system, systems, etc. for fracturing, seismic sensing, analysis of seismic data, assessment of one or more fractures, etc.

As an example, the geologic environment 150 and/or another geologic environment can include various types of features. For example, a geologic environment can include one or more salt domes, magma intrusions, volcanic regions, geothermal regions, waste storage regions, etc. As an example, a framework may provide for modeling geothermal phenomena, mechanical phenomena, waste storage phenomena (e.g., radioactive or other waste), etc. As an example, a geologic environment can include rock that may be oriented horizontally, vertically, or at other types of orientations. As an example, a geologic environment can include dikes and sills. As an example, a method can include identifying such features, for example, based at least in part on information acquired via one or more types of borehole tool sensors. As an example, a method can include identifying thinly bedded features that can disrupt the bedding such as veins, fractures, faults, dikes, sills, etc.

As mentioned, the system 100 may be used to perform one or more workflows. A workflow may be a process that includes a number of worksteps. A workstep may operate on data, for example, to create new data, to update existing data, etc. As an example, a may operate on one or more inputs and create one or more results, for example, based on one or more algorithms. As an example, a system may include a workflow editor for creation, editing, executing, etc. of a workflow. In such an example, the workflow editor may provide for selection of one or more pre-defined worksteps, one or more customized worksteps, etc. As an example, a workflow may be a workflow implementable in the TECHLOG framework or PETREL framework, for example, that operates on well log data, seismic data, seismic attribute(s), etc. As an example, a workflow may be a process implementable in the OCEAN framework. As an example, a workflow may include one or more worksteps that access a module such as a plug-in (e.g., external executable code, etc.).

FIG. 1 also shows one or more modules 198, which may operate in conjunction with the framework 170. For example, the one or more modules 198 may be implemented as one or more plug-in module, one or more external modules, etc. As an example, the one or more modules 198 may include one or more modules of the TECHLOG framework (Schlumberger Limited, Houston, Tex.), which can provide wellbore-centric, cross-domain workflows based on a data management layer. The TECHLOG framework includes features for petrophysics (core and log), geology, drilling, reservoir and production engineering, and geophysics.

Figure 2:
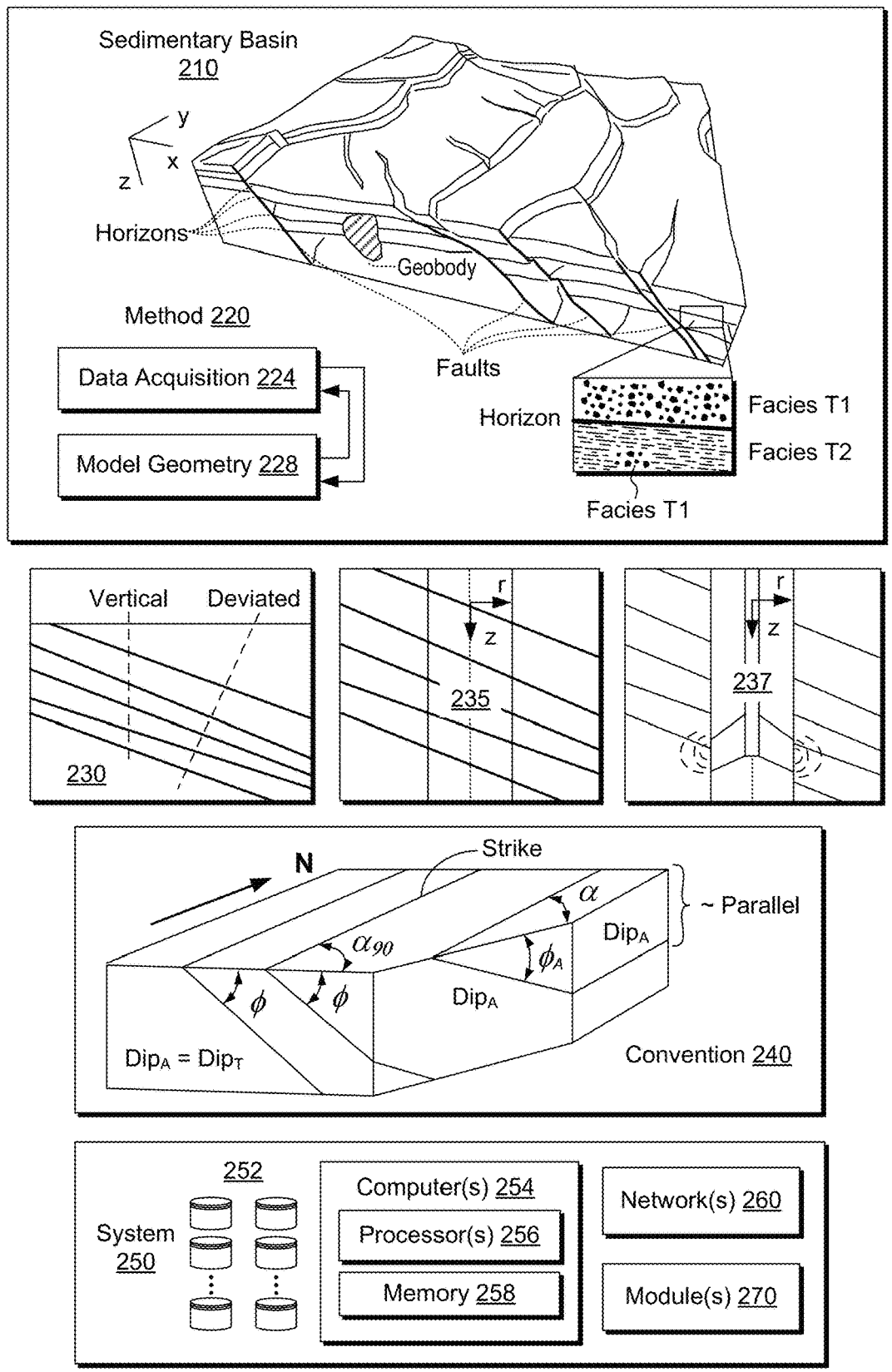
FIG. 2 illustrates examples of a basin, a convention and a system.

FIG. 2 shows an example of a sedimentary basin 210 (e.g., a geologic environment), an example of a method 220 for model building (e.g., for a simulator, etc.), an example of a formation 230, an example of a borehole 235 in a formation, an example of a convention 240 and an example of a system 250.

As an example, data acquisition, reservoir simulation, petroleum systems modeling, etc. may be applied to characterize various types of subsurface environments, including environments such as those of FIG. 1.

In FIG. 2, the sedimentary basin 210, which is a geologic environment, includes horizons, faults, one or more geobodies and facies formed over some period of geologic time. These features are distributed in two or three dimensions in space, for example, with respect to a Cartesian coordinate system (e.g., x, y and z) or other coordinate system (e.g., cylindrical, spherical, etc.). As shown, the model building method 220 includes a data acquisition block 224 and a model geometry block 228. Some data may be involved in building an initial model and, thereafter, the model may optionally be updated in response to model output, changes in time, physical phenomena, additional data, etc. As an example, data for modeling may include one or more of the following: depth or thickness maps and fault geometries and timing from seismic, remote-sensing, electromagnetic, gravity, outcrop and well log data. Furthermore, data may include depth and thickness maps stemming from facies variations (e.g., due to seismic unconformities) assumed to following geological events ("iso" times) and data may include lateral facies variations (e.g., due to lateral variation in sedimentation characteristics).

To proceed to modeling of geological processes, data may be provided, for example, data such as geochemical data (e.g., temperature, kerogen type, organic richness, etc.), timing data (e.g., from paleontology, radiometric dating, magnetic reversals, rock and fluid properties, etc.) and boundary condition data (e.g., heat-flow history, surface temperature, paleowater depth, etc.). Data can include nuclear data, for example, consider nuclear measurements as acquired by one or more tools, which can include one or more of electron density ($\rho_e$), hydrogen index (HI), and thermal neutron capture cross section ($\Sigma$).

In basin and petroleum systems modeling, quantities such as temperature, pressure and porosity distributions within the sediments may be modeled, for example, by solving partial differential equations (PDEs) using one or more numerical techniques. Modeling may also model geometry with respect to time, for example, to account for changes stemming from geological events (e.g., deposition of material, erosion of material, shifting of material, etc.).

The aforementioned modeling framework marketed as the PETROMOD framework (Schlumberger Limited, Houston, Tex.) includes features for input of various types of information (e.g., seismic, well, geological, etc.) to model evolution of a sedimentary basin. The PETROMOD framework provides for petroleum systems modeling via input of various data such as seismic data, well data and other geological data, for example, to model evolution of a sedimentary basin. The PETROMOD framework may predict if, and how, a reservoir has been charged with hydrocarbons, including, for example, the source and timing of hydrocarbon generation, migration routes, quantities, pore pressure and hydrocarbon type in the subsurface or at surface conditions. In combination with a framework such as the PETREL framework, workflows may be constructed to provide basin-to-prospect scale exploration solutions. Data exchange between frameworks can facilitate construction of models, analysis of data (e.g., PETROMOD framework data analyzed using PETREL framework capabilities), and coupling of workflows. As an example, the TECHLOG framework may be implemented in a workflow, for example, using one or more features for petrophysics (core and log), geology, drilling, reservoir and production engineering, and geophysics.

As shown in FIG. 2, the formation 230 includes a horizontal surface and various subsurface layers. As an example, a borehole may be vertical. As another example, a borehole may be deviated. In the example of FIG. 2, the borehole 235 may be considered a vertical borehole, for example, where the z-axis extends downwardly normal to the horizontal surface of the formation 230. As an example, a tool 237 may be positioned in a borehole, for example, to acquire information. As mentioned, a borehole tool may be configured to acquire electrical borehole images. As an example, the fullbore Formation MicroImager (FMI) tool (Schlumberger Limited, Houston, Tex.) can acquire borehole image data. A data acquisition sequence for such a tool can include running the tool into a borehole with acquisition pads closed, opening and pressing the pads against a wall of the borehole, delivering electrical current into the material defining the borehole while translating the tool in the borehole, and sensing current remotely, which is altered by interactions with the material.

Figure 3:
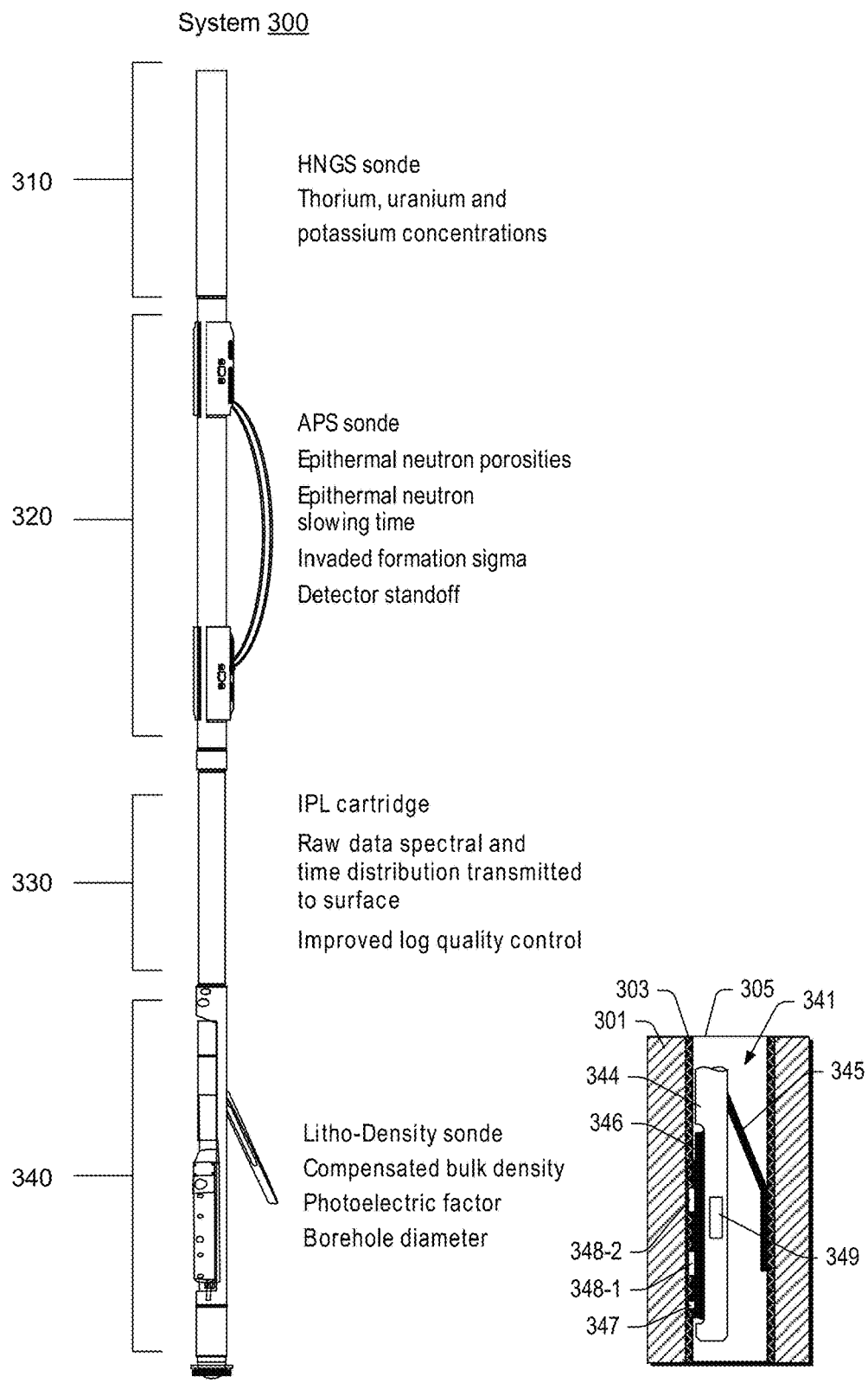
FIG. 3 illustrates an example of a system.

FIG. 3 shows an example of a system 300 that can include various assemblies. For example, the system 300 can include a hostile-environment natural gamma ray sonde (HNGS) assembly 310, an accelerator porosity sonde (APS) assembly 320, an integrated porosity lithology (IPL) cartridge assembly 330 and a litho-density sonde (LDS) assembly 340. As an example, the system 300 may be an integrated porosity lithology (IPL) system such as, for example, the IPL system marketed by Schlumberger Limited, Houston, Tex.

In the example of FIG. 3, the litho-density sonde (LDS) assembly 340 includes a pad with a gamma ray source and a plurality of detectors (e.g., two or more detectors). As an example, consider a Cesium-137 source, which emits gamma rays of about 0.66 MeV. As an example, detectors may be spaced, for example, axially along a LDS sonde. In the example of FIG. 3, the LDS assembly 340 can include magnetic shielding and electronic circuitry, for example, to record full pulse-height spectra from the detectors and process such information (e.g., into windows, etc.). In such an example, bulk density and photoelectric effect (PE) information may be derived. As an example, spectral information may be used to improve log and calibration quality control.

As an example, a tool such as an LDS assembly can include at least one detector and at least one source. As an example, a distance between a source and a detector may be of the order of inches. As an example, a tool that includes a source and detectors may have an axial length of about one meter or less as to a maximum axial length defined by locations of the source and the detectors.

As an example, a tool such as an LDS assembly can include circuitry where the circuitry includes at least one controller (e.g., microcontroller, processor, etc.). As an example, the LDS assembly may include memory that can store instructions executable by at least one controller (e.g., consider executable firmware, software, etc.). As an example, one or more filters may be included in an LDS assembly and/or in a unit operatively coupled to an LDS assembly. In such an example, the one or more filters may be applied to data acquired via one or more detectors. As an example, a detector may have an associated filter or filter set. For example, where an LDS assembly includes N detectors, N filters or N sets of filters may be provided (e.g., in hardware, software, hardware and software).

As an example, the LDS assembly 340 can include a specified range for bulk density measurements (e.g., about 2 g/cm$^3$ to about 3 g/cm$^3$ with an accuracy of about +/−0.01 g/cm$^3$) and a specified range for photoelectric factor (PE factor) (e.g., about 1 to about 6, with an accuracy of about +/−10 percent).

FIG. 3 also shows an example of another LDS assembly 341 in a view next to the LDS assembly 340 with respect to a formation 301 that may include mudcake 303 in a borehole 305. The LDS assembly 341 can include various features of the LDS assembly 340, either of which can be part of a downhole tool such as, for example, the tool 237 of FIG. 2, the logging string 540 of FIG. 5, the tool 1708 of FIG. 17; noting that the tool 1708 can include features of a tool or tools as in, for example, FIG. 3, FIG. 5, etc. As shown in the example, the LDS assembly 341 can include a body or housing 344, a plough 346, an arm 345, a source 347, a plurality of detectors 348-1 and 348-2 (e.g., two or more detectors), and circuitry 349. As an example, the circuitry 349 may include one or more controllers, memory, etc. As an example, a controller may be a microcontroller (e.g., an ARM chip, etc.), a processor, an ASIC, etc. As an example, a controller may operate via instructions stored in memory (e.g., firmware instructions, software instructions, RISC instructions, etc.). As an example, circuitry may be included in a cartridge such as, for example, the cartridge assembly 330 of the system 300 of FIG. 3. As an example, one or more of the assemblies 310, 320, 330 and 340 of the system 300 may include interfaces, for example, for communication of information. As an example, one or more of the assemblies 310, 320, 330 and 340 of the system 300 may include memory, for example, as a storage device that may store one or more of data and instructions. As an example, a method may be implemented in part via instructions that may be executable by circuitry (e.g., a controller, microcontroller, processor, etc.).

As an example, a tool such as the NEOSCOPE tool (Schlumberger Limited, Houston, Tex.) may be utilized to acquire measurements. Such a tool can include circuitry for making one or more of neutron porosity and neutron gamma density measurements. Such a tool may be a formation evaluation while drilling tool. As an example, a tool can include circuitry that generates neutron pulses on demand without a radio-isotopic or gamma-ray source. Such circuitry can be referred to as a pulsed neutron generator (PNG). As an example, a tool that includes a PNG and associated detector(s) can be utilized to determine the hydrogen index (HI) of material such as a formation where high-energy neutrons are slowed down by hydrogen atoms in the formation. Measurements can use count rates from near and far helium-3 tubes to determine thermal neutron porosity and HI. As to sigma, it can be utilized to provide a resistivity-independent formation saturation evaluation, for example, to help distinguish formation fluid types and/or to identify a low-resistivity pay zone while drilling. As an example, a tool can include memory and a processor, as well as, for example, a power source (e.g., a battery, a generator, etc.) and/or one or more power source interfaces. As an example, a tool may have a cross-sectional dimension that makes it suitable for use in boreholes with sizes from about 6 inches (e.g., 15 cm) to about 18 inches (e.g., about 45 cm).

As an example, a tool such as the ECOSCOPE tool (Schlumberger Limited, Houston, Tex.) may be utilized to acquire measurements. Such a tool can include one or more PNGs and associated detectors. Such a tool can include features for one or more of resistivity, neutron porosity, azimuthal gamma ray, density, elemental capture spectroscopy and sigma measurements. Such a tool can be operatively coupled to one or more telemetry systems that may provide for real-time acquisition and, for example, real-time decision making, rendering of graphics, etc.

As mentioned, nuclear measurements may be acquired by one or more tools where such nuclear measurements can include one or more of electron density ($\rho_e$), hydrogen index (HI), and thermal neutron capture cross section ($\Sigma$).

As an example, a tool can include features that can measure, directly and/or indirectly, electron density, which can be a measurement of the bulk density of the formation, based on the reduction in gamma ray flux between a source and a detector due to Compton scattering. For example, consider a gamma ray source such as a $^{137}$Cs (cesium) source chosen so that gamma ray energies are high enough to interact by Compton scattering but not by pair production; or, for example, consider a PNG. In a tool, detectors can discriminate against low gamma ray energies that may have been influenced by photoelectric absorption. Although Compton scattering depends on electron density and not bulk density, density logs are calibrated to give the bulk density in various sedimentary rocks. Due to the Z/A effect there can be small differences in some formations. A measurement responds to the average density of the material between source and detector. In a wireline measurement, care can be taken to minimize mud between sensors and formation, for example, by pressing a pad against a borehole wall, with source and detector focused into the formation. In logging-while-drilling measurement, a sleeve may be mounted on a collar around sensors to exclude mud. Detectors can measure gamma rays scattered from a formation; noting that mudcake or borehole rugosity can affect measurements. As an example, to compensate for mudcake, a tool may provide two or more detectors at different spacings.

As an example, a tool can include features that can measure, directly and/or indirectly, hydrogen index (HI), which represents the number of hydrogen atoms per unit volume divided by the number of hydrogen atoms per unit volume of pure water at surface conditions. The hydrogen index (HI) is thus the density of hydrogen relative to that of water. The HI is a factor in the response of a neutron porosity log.

As an example, a tool can include features that can measure, directly and/or indirectly, sigma ($\Sigma$), which is the macroscopic cross section for the absorption of thermal neutrons, or capture cross section, of a volume of matter, measured in capture units (c.u.). Sigma is also used as an adjective to refer to a log of this quantity. Sigma can be the principal output of a pulsed neutron capture log, which may be used, for example, to determine water saturation behind casing. Thermal neutrons tend to have about the same energy as that of surrounding matter (e.g., less than approximately 0.4 eV).

Figure 4:
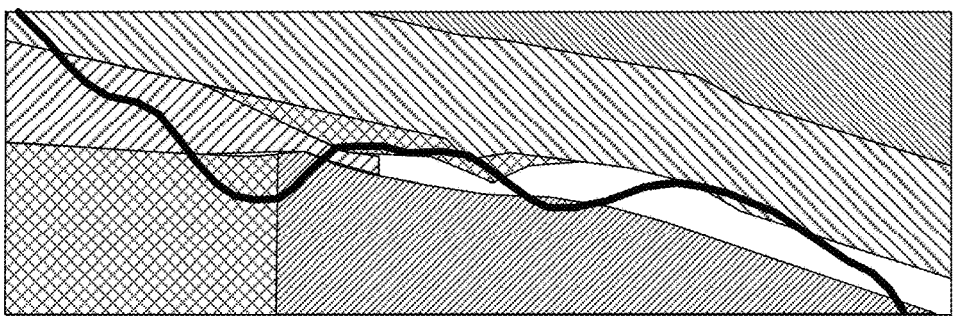
FIG. 4 illustrates an example of a graphical user interface system.
Figure 4:
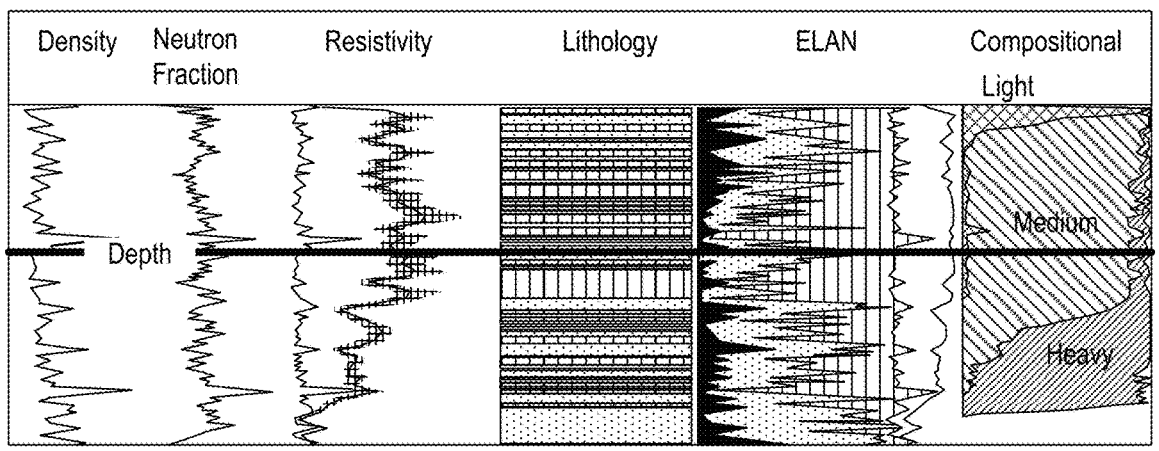
Figure 4:
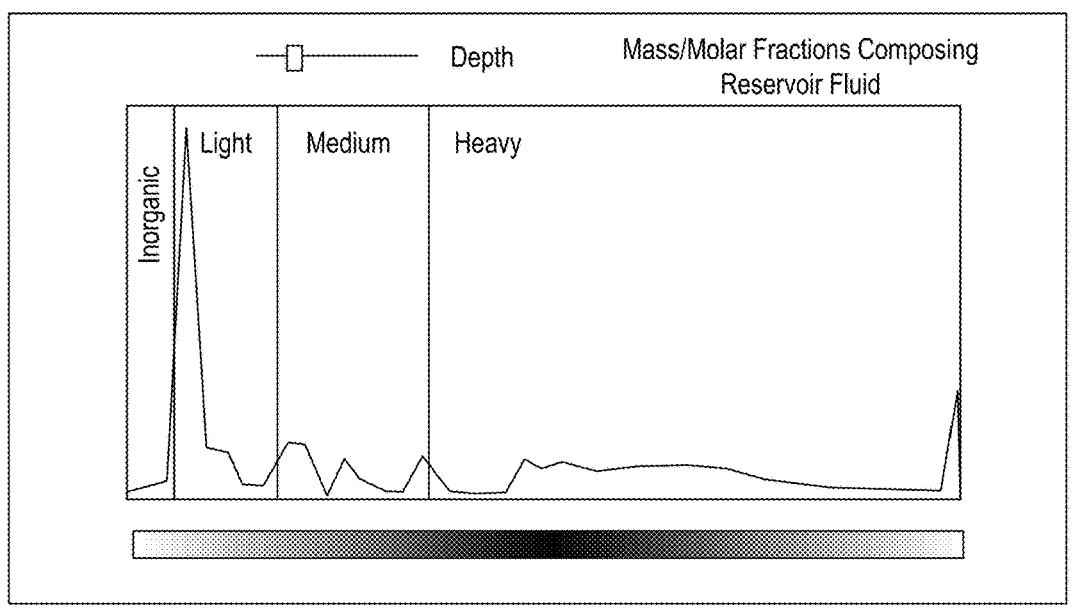

FIG. 4 shows an example of a graphical user interface (GUI) system 400 that can include instructions for rendering various GUIs to a display, which can be interactive and responsive to input, whether via receipt of measurement data from one or more sensors, via receipt of user input from one or more input devices, via automated execution of instructions by a processor, etc.

In the example of FIG. 4, a GUI 405, a GUI 410 and a GUI 430 are shown. The GUI 405 includes a layered earth model rendered as a slice through a three-dimensional space of the earth (e.g., a region of interest). As shown, the layered earth model includes various regions that can be categorized according to various properties (e.g., properties of material or materials). Such a model can be a stratigraphic model that includes various stratigraphic properties. Stratigraphy includes the study of the history, composition, relative ages and distribution of strata, and the interpretation of strata to elucidate Earth history. The comparison, or correlation, of separated strata can include study of their lithology, fossil content, and relative or absolute age, or lithostratigraphy, biostratigraphy, and chronostratigraphy. The GUI 405 further includes a trajectory in multiple dimensions of a borehole in the Earth that penetrates one or more portions of one or more reservoirs. A borehole can be a drilled hole or borehole, including the openhole or uncased portion. A borehole may refer to the inside diameter of a bore wall, for example, a rock face that bounds a drilled hole. As an example, the trajectory of the GUI 405 can include measurements such as measured depth, which may be from a surface, an interface, etc. As an example, the measured depth may be in feet, meters, etc. As an example, a portion of the trajectory may be a planned portion that is yet to be drilled and which may be adjusted based on one or more analyses, outputs, etc., optionally from measurements during wireline services, during drilling, etc.

The GUI 410 includes measurements and property values of a reservoir with respect to depth (vertical axis). As an example, the depth may correspond to true vertical depth (TVD) and/or measured depth (MD), for example, as associated with an actual and/or a planned trajectory of a borehole. As shown, the GUI 410 can include density measurements, neutron fraction measurements, lithology values, elemental analysis values, and compositional values, which may be for light, medium and heavy components of reservoir fluid. As shown, a horizontal line indicates a particular depth. The GUI 430 shows a depth slider control that may be utilized to control the horizontal line and hence select a particular depth. In response to depth selection, whether manual or automated, a plot of mass and/or molar fractions of components of reservoir fluid can be generated and rendered. For example, consider the horizontal line as crossing the compositional window of the GUI 410, which shows light, medium and heavy hydrocarbon components. As shown, a component can be an inorganic component. Thus, at a particular depth, a mixture of inorganic and organic components (e.g., hydrocarbon components) may be present.

As explained, nuclear parameters can be sensitive to the hydrocarbon type. As an example, a method can include acquiring nuclear measurements and determining the hydrocarbon type using at least a portion of those acquired measurements. As an example, such a method can include determining hydrocarbon fluid properties, for example, in addition to a volume vector. As an example, a method can include computing a compositional log that includes hydrocarbon type versus depth where the compositional log includes values that are determined using acquired nuclear measurements, which may be accessed from a data storage device or, for example, acquired in real-time during a field operation that utilizes one or more downhole tools. For example, a logging operation can be performed that acquires various nuclear measurements that can be processed to compute a compositional log.

Various frameworks can be limited in their abilities to provide values as to composition. For sequential and non-linear simultaneous computational solvers to compute a solution for formation volume, the following can be demanded as inputs: knowledge of logging tools physics and response; knowledge of the environment; and some knowledge of what is a reasonable result. In such an approach, sources of error can include: fluid type to solve for (gas and/or oil); fluid properties (end points) inconsistency; and composition of hydrocarbons being under-determined.

As explained, nuclear measurements can be sensitive to hydrocarbon composition. Thus, as an example, a method can include implementing a combination of multi-physics inversion framework and hydrocarbon composition estimation using nuclear measurements. Such an approach can help to mitigate situations where hydrocarbon composition is under-determined. As explained with respect to FIG. 4, a computational framework can include computing estimates of reservoir fluid composition using nuclear measurements and rendering those estimates to a display, for example, using one or more GUIs that allow for user interaction and/or live updates responsive to acquisition of one or more measurements.

As an example, a method can include generating multi-dimensional graphics that include a coordinate system with axes that correspond to nuclear properties (e.g., nuclear parameter values). For example, consider a coordinate system with at least two of the following nuclear properties: electron density, hydrogen index and sigma. In such a coordinate system, a method can include clustering where a cluster represents a particular fluid type in a multi-dimensional space as defined by two or more nuclear properties. As an example, in a three-dimensional space, a series of clusters may extend substantially along a linear path where the axes are linear axes for electron density, hydrogen index and sigma. In such an example, clusters may correspond to dry gas, wet gas, gas condensate, volatile oil, black oil, heavy oil, super heavy oil and asphaltene-rich black oil. While the foregoing list includes seven different types of fluid, a method may include a different scheme as to a different number of types of fluids (e.g., from two fluid types to more than ten fluid types). As an example, a method can include determining an optimum number of types of fluids for purposes of clustering (e.g., cluster identification). As an example, such a method may be utilized, for example, for purposes of generating a compositional log, which may be rendered to a display as part of a graphical user interface (GUI). As an example, a coordinate system may include an electron density axis in grams per cubic centimeter that ranges from approximately 0.2 to approximately 1.4; a hydrogen index axis that ranges from approximately 0.2 to approximately 1.6; and a sigma axis in c.u. that ranges from approximately 12 to approximately 40. Such axes can define a multi-dimensional space where clusters can be rendered therein where each cluster represents a different type of fluid. As an example, a method can utilize multiple coordinates (e.g., axes) where each coordinate (e.g., axis) has a corresponding relationship to hydrocarbons in a mixture, for example, each coordinate can be for a parameter that is sensitive to the composition of hydrocarbons in a mixture (e.g., a fluid mixture such as a reservoir fluid).

As an example, a type of fluid may depend at least in part on number of components of a certain type. For example, consider alkane molecules, which may range in number from 1 to more than 30 and, for example, which may be arranged in different types of structures (e.g., linear, cyclic, etc.). As an example, molecules such as nitrogen, hydrogen, and oxygen may be utilized to define a type of fluid, optionally in one or more combinations, which may or may not include hydrocarbons.

As an example, a method can include using mole fraction or molar fraction, which can be defined as the amount of a constituent (expressed in moles) divided by the total amount of constituents in a mixture (also expressed in moles). As an example, a method can include using mass fraction of a substance within a mixture via mass of a substance to the total mass of a mixture. As an example, a method can include using volume fraction, which can be defined as the volume of a constituent divided by the volume of constituents of a mixture, for example, prior to mixing. As an example, a method can include accounting for volume of mixing of various constituents.

As an example, a method can include receiving data points defined in space where each data point represents a particular sample of fluid. In such an example, the method can include computing one or more centroids of a selected number of data points.

As an example, a method can include utilizing a computational framework that includes at least one processor configured for estimating fractions of hydrocarbon components in a given reservoir fluid mixture based on the nuclear measurements from one or more tools. For example, consider one or more of the aforementioned tools or features thereof (e.g., NEOSCOPE tool, ECOSCOPE tool, PNG, etc.).

As an example, a method can include generating and/or acquiring data. As an example, data may be in the form of a database stored using digital data storage equipment (e.g., drives, servers, etc.). As an example, a database can include compositional and flash data for more than 100 fluid samples from one or more reservoirs. As an example, such fluid samples may be subjected to gas chromatography analysis to generate data. As an example, a method can include processing such data using a computational framework where such processing can include clustering. For example, consider a method that includes clustering data from fluid samples according to their compositional distribution and, for example, as averaged around their centroids. As an example, a method can assess such clusters, for example, via classifying that classifies the clusters into a plurality of distinct fluid types (e.g., hydrocarbon, etc.). As explained below, for example, with respect to FIG. 7, a method can include utilizing defined fluid types for performing flash computations.

As an example, a method can include assessing a database of hundreds of reservoir fluid samples (e.g., fluid mixtures) that have associated compositional data and flash analysis data available. In such a method, a flash simulation framework can be used to compute density at downhole conditions for these fluid mixtures and the results can be compared and analyzed statistically against measured mixture compositions (e.g., as may be provided by a laboratory). In such an approach, gas chromatography analysis of these reservoir fluid samples can be mined and the reservoir fluid samples clustered according to their compositional distribution and averaged around their centroids. These clusters can then be classified into distinct hydrocarbon fluid types (e.g., dry gas (DG), wet gas (WG), gas condensate (GC), volatile oil (VO), black oil (BO), heavy oil (HO), super heavy oil (SHO), asphaltenes-rich oil (ASP), etc.). Such an approach can include assessing one or more equations of state (EoSs). As an example, for each fluid type, an EOS-predicted downhole mixture density at a formation pressure and a formation temperature can then be used in a nuclear forward modeling program that converts the mixture composition and mixture density to nuclear parameters values for nuclear parameters such as electron density ($\rho_e$), hydrogen index (HI), and thermal neutron capture cross section ($\Sigma$).

As an example, a method can include executing a computational framework that includes at least one processor for determining composition properties of one or more types of fluids. For example, consider a framework that includes the PVTz analysis software (Schlumberger Limited, Houston, Tex.). Such a framework can process laboratory measured PVT data for fluids. For example, such a framework can record fluid phase behavior during PVT lab analyses. As an example, such a framework can be operatively coupled to lab equipment to use position and other types of data (e.g., piston position to compute volumes). Such a framework can perform material balance calculations, equilibrium checks, oil-based mud contamination assessments, etc. As an example, such a framework can perform flash calculations. Such a framework may implement one or more different equations of state (EoS). As an example, an ECLIPSE simulator compositional simulation E300 flash package may be utilized (e.g., PVTToolbox) to compute densities at various downhole conditions for various fluid types, for example, using the 3-parameter Peng Robinson adjusted EoS or, for example, one or more other EoSs.

As to the Peng Robinson EoS, it aims to provide a framework where parameters can be expressible in terms of critical properties and the acentric factor; the model can provide reasonable accuracy near the critical point, particularly for calculations of the compressibility factor and liquid density; mixing rules can be formulated to not employ more than a single binary interaction parameter, which can be independent of temperature, pressure and composition; and the equation can be applicable to calculations of fluid properties in natural gas processes.

The Peng Robinson EoS may be represented as follows:

$$p = \frac{RT}{V_m - b} - \frac{a\alpha}{V_m^2 + 2bV_m - b^2}$$

$$a \approx 0.45724 \frac{R^2 T_c^2}{p_c}$$

$$b \approx 0.07780 \frac{RT_c}{p_c}$$

$$\alpha = (1 + \kappa(1 - T_r^{0.5}))^2$$

$$\kappa \approx 0.37464 + 1.5226\omega - 0.26992\omega^2$$

$$T_r = T/T_c$$

Above, $V_m$ is molar volume and the subscript "c" represents critical, and, in polynomial form as function of the compressibility factor Z, the Peng Robinson EoS may be presented as follows:

$$A = \frac{\alpha a p}{R^2 T^2}$$

$$B = \frac{bp}{RT}$$

$$Z^3 - (1 - B)Z^2 + (A - 2B - 3B^2)Z - (AB - B^2 - B^3) = 0$$

$$Z = \frac{PV}{nRT}$$

As to some other examples, a method or system may utilize the Redlich-Kwong EoS, the Soave modification of the Redlich-Kwong (SRK) EoS, the SRK with volume translation of Peneloux (SRK-P), or another EoS formulation. As to the Soave modification of the Redlich-Kwong (SRK) EoS, consider the following equations:

$$p = \frac{RT}{V_m - b} - \frac{a\alpha}{V_m(V_m + b)}$$

-continued $$a \approx 0.42747 \frac{R^2 T_c^2}{P_c}$$

$$b \approx 0.08664 \frac{RT_c}{P_c}$$

$$\alpha = (1 + \kappa(1 - T_r^{0.5}))^2$$

$$\kappa \approx 0.48508 + 1.55171\omega - 0.15613\omega^2$$

$$T_r = T/T_c$$

As to the SRK, consider a short-hand representation as follows:

$$p = \frac{RT}{V_{m,SRK} - b} - \frac{\alpha}{V_{m,SRK}(V_{m,SRK} + b)}$$

$$a = a_c \alpha$$

$$a_c \approx 0.42747 \frac{R^2 T_c^2}{P_c}$$

$$b \approx 0.08664 \frac{RT_c}{P_c}$$

As to SRK-P, a factor "c" is introduced, which is a parameter of individual fluid components that can be estimated by a correlation that includes a Rackett compressibility factor ($Z_{RA}$). For example, consider:

$$c_i \approx 0.40768 \frac{RT_{ci}}{P_{ci}} (0.29441 - 0.29056 - 0.08775\omega_i)$$

In SRK-P, c can be summed for a number of components and it can be utilized to replace or supplement the factor "b" of SRK (e.g., b replaced by c, a sum of b and c or b minus c).

As to PVT analyses, it can provide output as to how fluids behave within a reservoir, within the wells, at surface conditions, in a conduit network, at a refinery, etc. A method can call for various fluid properties to be estimated or known over a range of temperatures and/or a range of pressures. As an example, when gas is injected into a reservoir, a method can include determining how properties of the original reservoir fluid will change as the composition changes.

PVT analyses as to fluid properties can help with predictions as to one or more of the following: the composition of well stream as a function of time; completion design, which depends on the properties of the wellbore; liquids; whether to inject or re-inject gas, and if so, the detailed specification of the injected gas; how much C3, C4, C5's to leave in; separator configuration and stage for injection gas; miscibility effects that may result from the injected gas; amounts and composition of liquids left behind and their properties: density, surface tension, viscosity, etc.; separator/NGL plant specifications; $H_2S$ and $N_2$ concentration in produced gas; product values versus time; etc.

As to compositional simulation using a simulator, it can provide output that is improved with respect to black-oil simulation. Composition simulation output can provide improved description of reservoir processes in a number of situations. For example, compositional simulation can assist in Enhanced Oil Recovery (EOR) processes that involves a miscible displacement; cases where gas injection/re-injection into an oil produces a large compositional changes in the fluids; if condensates are recovered using gas cycling (injected gas is substantially different from the composition of free gas in the reservoir); surface facilities detailed compositions of one or more production streams; times and timings; oil production rate(s); etc. Composition simulation can provide insight as to phase behavior; multi-contact miscibility; immiscible or near-miscible displacement behavior in compositionally dependent mechanisms such as vaporization, condensation, and oil swelling; composition-dependent phase properties such as viscosity and density on miscible sweep-out; and interfacial tension (IFT) especially the effect of IFT on residual oil saturation. Such effects can have a substantial effect on production of one or more resources from a reservoir or reservoirs.

In a black-oil approach, a fluid may be fully described by fluid properties in a table of property versus pressure; whereas, in a compositional approach, a solver is utilized to solve a flash equation and solve an EoS.

In a multi-physics inversion model, the equation of state predicted downhole mixture density at the formation pressure and temperature for each fluid type can be used in a computational framework (e.g., a SNUPAR computational framework, etc.) that converts the mixture composition and mixture density to nuclear parameters such as electron density index ($\rho_e$), hydrogen index (HI), and thermal neutron capture cross section ($\Sigma$).

The multi-physics inversion framework can invert for the downhole reservoir fluid properties of electron density, HI, and sigma using measurements acquired by one or more tools. As an example, a system can include a model that then estimates the mass fractions of hydrocarbon components of a given reservoir fluid mixture by spatial distance calculations of the inverted log derived mixture properties to the fluid types EoS derived properties. As an example, a system can generate a composition log for an interval of interest. Such a log may be continuous, discrete or a combination of continuous portion(s) and discrete portion(s).

As an example, a system can compute nuclear parameters for reservoir fluids using a framework such as the SNUPAR framework, which takes as input the composition and density of the fluid of interest. Large changes in the density of hydrocarbon fluids at different pressures and temperatures make the computation of the volumetric and phase behavior of mixtures at reservoir pressure and temperature one of the processes in the workflow. Such a workflow can use an equation of state (EoS) approach to determine the density of each fluid type at reservoir pressure and temperature.

The SNUPAR framework can calculate nuclear measurement parameters for mixtures of elements found in nuclear geophysics applications. Parameters calculated can include the neutron slowing-down length, the thermal neutron diffusion length, the thermal neutron capture cross-section, the formation density, the electron density index, the volumetric photoelectric absorption coefficient, and the effective atomic number. The SNUPAR framework has been benchmarked with published laboratory measurements and with results from the Monte Carlo neutron photon computations. One or more approaches may be utilized to handle variations in salinity of formation water. As an example, a workflow can utilize a modified migration-length model to describe the thermal neutron response to a compensated neutron log. Some examples of applications of the SNUPAR framework for determining reservoir gas saturation, carbon-dioxide saturation in an enhanced oil recovery project, and the effects of mineral mixtures on neutron log response are presented herein.

As mentioned, a system may include utilizing one or more tools in the field and generating one or more compositional logs, optionally during use of such one or more tools. As an example, a tool may be a drilling tool, a wireline service tool or another type of tool.

Figure 5:
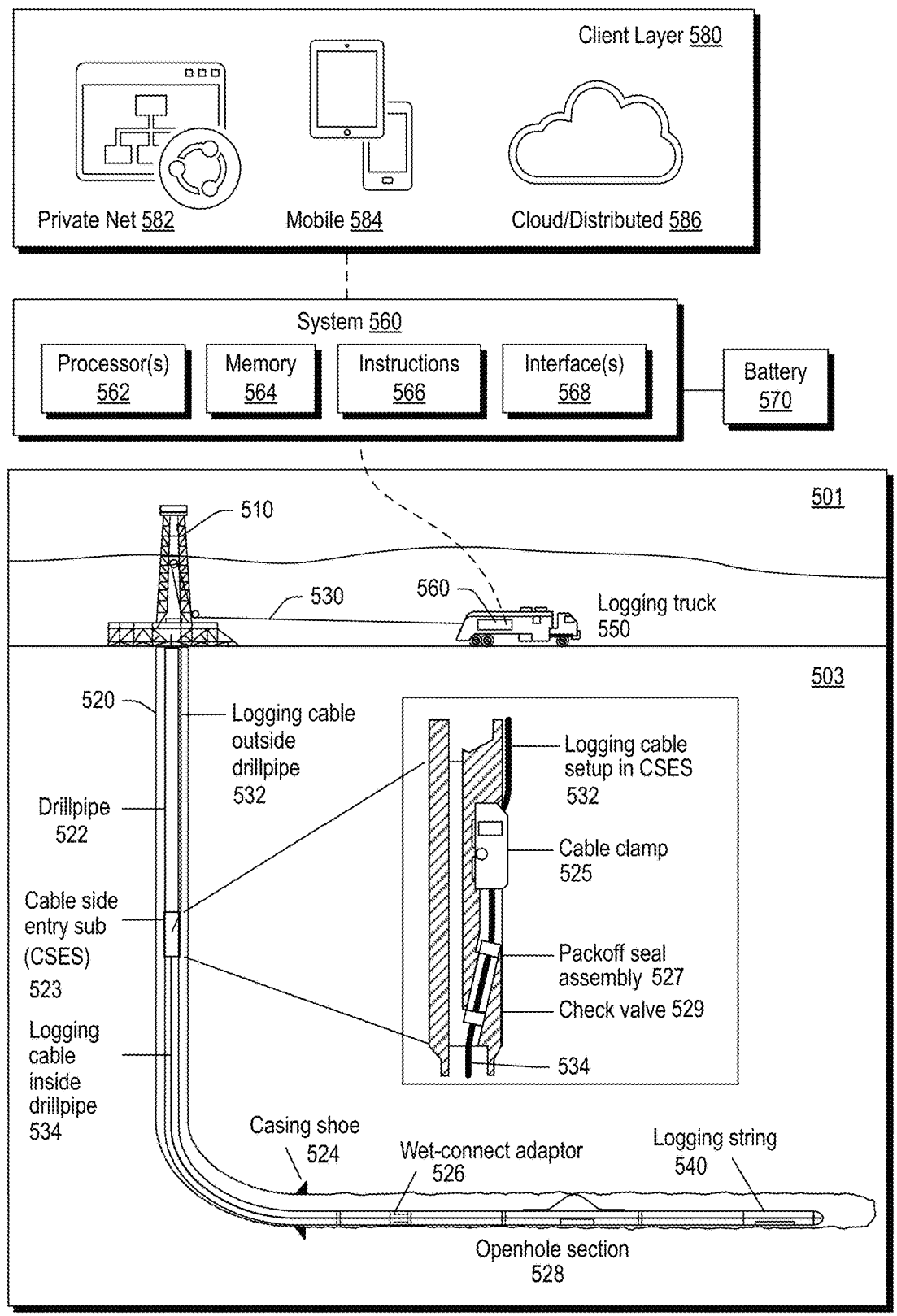
FIG. 5 illustrates an example of a system.

FIG. 5 shows an example of an environment 501 that includes a subterranean portion 503 where a rig 510 is positioned at a surface location above a bore 520. In the example of FIG. 5, various wirelines services equipment can be operated to perform one or more wirelines services including, for example, acquisition of data from one or more positions within the bore 520. As an example, one or more tools may be utilized for performing one or more wireline operations (e.g., services, etc.). A tool may be referred to as a logging tool, which may be part of a logging string that can be positioned, conveyed, etc., in a bore for acquiring data pertaining to an environment (e.g., a formation, a casing, cement, fluid(s), etc.). As an example, one or more features of the system 300, one or more features of the GUI system 400, etc., may be utilized in conjunction with one or more of the pieces of equipment shown in FIG. 5.

In the example of FIG. 5, the bore 520 includes drillpipe 522, a casing shoe, a cable side entry sub (CSES) 523, a wet-connector adaptor 526 and an openhole section 528. As an example, the bore 520 can be a vertical bore or a deviated bore where one or more portions of the bore may be vertical and one or more portions of the bore may be deviated, including substantially horizontal.

In the example of FIG. 5, the CSES 523 includes a cable clamp 525, a packoff seal assembly 527 and a check valve 529. These components can provide for insertion of a logging cable 530 that includes a portion 532 that runs outside the drillpipe 522 to be inserted into the drillpipe 522 such that at least a portion 534 of the logging cable runs inside the drillpipe 522. In the example of FIG. 5, the logging cable 530 runs past the wet-connect adaptor 526 and into the openhole section 528 to a logging string 540.

As shown in the example of FIG. 5, a logging truck 550 (e.g., a wirelines services vehicle) can deploy the wireline 530 under control of a system 560. As shown in the example of FIG. 5, the system 560 can include one or more processors 562, memory 564 operatively coupled to at least one of the one or more processors 562, instructions 566 that can be, for example, stored in the memory 564, and one or more interfaces 568. As an example, the system 560 can include one or more processor-readable media that include processor-executable instructions executable by at least one of the one or more processors 562 to cause the system 560 to control one or more aspects of equipment of the logging string 540 and/or the logging truck 550. In such an example, the memory 564 can be or include the one or more processor-readable media where the processor-executable instructions can be or include instructions. As an example, a processor-readable medium can be a computer-readable storage medium that is not a signal and that is not a carrier wave.

FIG. 5 also shows a battery 570 that may be operatively coupled to the system 560, for example, to power the system 560. As an example, the battery 570 may be a back-up battery that operates when another power supply is unavailable for powering the system 560 (e.g., via a generator of the wirelines truck 550, a separate generator, a power line, etc.). As an example, the battery 570 may be operatively coupled to a network, which may be a cloud network. As an example, the battery 570 can include smart battery circuitry and may be operatively coupled to one or more pieces of equipment via a SMBus or other type of bus.

As an example, the system 560 can be operatively coupled to a client layer 580. In the example of FIG. 5, the client layer 580 can include features that allow for access and interactions via one or more private networks 582, one or more mobile platforms and/or mobile networks 584 and via the "cloud" 586, which may be considered to include distributed equipment that forms a network such as a network of networks. As an example, the system 560 can include circuitry to establish a plurality of connections (e.g., sessions). As an example, connections may be via one or more types of networks. As an example, connections may be client-server types of connections where the system 560 operates as a server in a client-server architecture. For example, clients may log-in to the system 560 where multiple clients may be handled, optionally simultaneously.

An approach to determining in-situ hydrocarbon composition from log measurements can include first assuming that a hydrocarbon type is present (gas, oil), then assigning log parameters to the hydrocarbon phase, and, finally, using a minimization technique to solve for hydrocarbons volume. Such an approach can be problematic as the various log properties assigned are generally not rigorously constrained to be consistent with respect to the composition of the hydrocarbon or the downhole pressure and temperature. Such an approach generally involves use of a database of log parameters for various hydrocarbon fluid types at downhole pressures and temperatures.

As an example, a workflow can include assessing a database of hundreds of reservoir samples from one or more reservoirs (e.g., regional, globally, etc.) for compositional data and, for example, performing one or more flash analyses. For example, consider a flash calculation framework that can be implemented to compute density at downhole conditions for various fluid mixtures as may be present in such a database or databases to generate results. In such an example, a workflow can include comparing and analyzing (e.g., statistically) various results against measured mixture compositions, for example, as may be provided by a laboratory.

As an example, a workflow can include accessing and/or generating gas chromatography data, for example, via analyses of samples. As an example, a workflow can include clustering, for example, clustering samples according to sample data (e.g., physical data, chemical data, descriptions, etc.) such that clusters are formed according to their compositional distribution as may be, for example, averaged around their centroids. A workflow can include, for example, classifying using cluster information (e.g., cluster characteristics). As an example, consider classifying clusters into distinct hydrocarbon fluid types (e.g., DG, WG, GC, VO, BO, HO, SHO, ASP, etc.).

In various example trials, performance of six different equations of state (EoS) was compared. Various results show that the three-parameter Soave-Redlich-Kwong (SRK) EoS with Peneloux's correction (SRK-P) yielded results that tended to be more accurate than others.

As an example, a workflow can, for each fluid type, utilize EoS-predicted downhole mixture density at the formation pressure and temperature in a nuclear forward modeling framework that operates to convert mixture composition and mixture density to nuclear parameters values such as, for example, values for one or more of the following nuclear parameters electron density ($\rho_e$), hydrogen index (HI), and thermal neutron capture cross section ($\Sigma$).

As an example, a workflow can be implemented using a computational system that includes circuitry (e.g., hardware and executable instructions) to determine the nuclear log properties (e.g., nuclear parameter values), while assuring the properties' consistency to each other for given fluid type(s), reservoir pressure(s), and temperature(s).

As mentioned, a workflow can generate data within a multi-dimensional space (e.g., n-dimensional space). For example, consider a workflow that takes reservoir hydrocarbon fluid nuclear properties and uses two or more of them together in an n-dimensional space to predict the hydrocarbon composition.

As an example, a workflow can include performing a multiphysics inversion to invert for downhole reservoir fluid electron density, HI, and $\Sigma$ using wireline measurements and/or LWD measurements.

As an example, a workflow can include model-based estimating of mass fractions (e.g., or mole fractions) of each hydrocarbon component of a reservoir fluid mixture by calculating spatial distance (e.g., via a multivariate interpolation) between reservoir fluid nuclear properties and fluid types EoS-derived properties. Such a workflow can generate a composition log (or compositional log), which may be, for example, a continuous composition log for an entire interval of interest. In such an example, an EoS can be utilized to predict fluid densities and then properties can be computed as to the type of hydrocarbons and their volumes with a multiphysics inversion. For example, an EoS can serve to compute fluid mixtures' densities at P, T, which can then be input along with the mixture composition in a forward modeling tool (SNUPAR VC3) to compute the fluid mixtures' nuclear properties (e.g., nuclear parameter values).

To extract considerable value from measurements, petrophysical interpretation analyses can be performed that account for effects such as, for example, one or more of invasion, formation layering and dip, while addressing geometry effects observed such as, for example, one or more of adjacent bed boundaries and polarization horns. Such an approach can be beneficial for high angle and horizontal wells, which tend to pose challenges to conventional approach to formation evaluation.

As an example, a workflow can address such concerns via constructing a layered earth model, which may be used, for example, in an iterative (e.g., model-compare-update or automatic inversion) workflow to deliver an invasion and geometry adjusted properties for one or more modeled layers. As an example, such a workflow can output an adjusted layered earth model as a validated representation of the subsurface layering and formation properties. As an example, a layered earth model such as the layered earth model of the GUI 405 may be utilized. Such a model can be a layered earth model with geometrically adjusted petrophysical log properties. As an example, for a set of nuclear measurements, layer proprieties electron density ($\rho_e$), hydrogen index (HI), and thermal neutron capture cross section ($\Sigma$), can be used in inversion techniques to solve for the reservoir fluid volumes, through a cost function minimization method. Such an approach assumes that a hydrocarbon type is present and assigns log parameters to the type to be solved. The density of the hydrocarbon phase, if not manually assigned, is usually computed by interpolating, for a given temperature and pressure, PVT proprieties calculated by black oil correlations. Such an approach demands knowledge a priori of reservoir fluid type to be solved for, constraining the solution to this choice, and allows log parameters assigned to be inconsistent to each other and to the composition of the hydrocarbon at the pressure and temperature of the reservoir.

As an example, a workflow can include accessing and/or generating one or more spectroscopy logs and/or resistivity logs, which may facilitate solving for more unknowns. As an example, given a relatively comprehensive set of measurements, a new multiphysics inversion model can solve for in-situ reservoir fluid volume and reservoir fluid nuclear parameters (e.g., optionally simultaneously).

As an example, log measurements, including contributions from rock matrix, hydrocarbon, and brine, may be used in an inversion framework for reservoir fluid properties that employs response equations in terms of formation volumes and sensitivity maps in terms of formation physical properties. As an example, a computational framework can be implemented to obtain HI, $\rho_e$, and $\Sigma$ for hydrocarbons, while maintaining consistency between various log parameters. Such log derived nuclear properties can be generated to represent the fluid properties at reservoir pressure and temperature. As mentioned, a workflow can include determining nuclear properties of certain predefined hydrocarbon "types" to reservoir temperature and pressure to compare them to log derived downhole fluid properties. For example, nuclear parameters for reservoir fluids can be computed by a computational framework such as the SNUPAR framework that takes as input the composition and density of the fluid of interest. Large changes in the density of hydrocarbon fluids at different pressures and temperatures make the computation of the volumetric and phase behavior of mixtures at reservoir pressure and temperature a desirable process in such a workflow. As an example, an equation of state (EoS) approach can be implemented to determine the density of each fluid type at reservoir pressure and temperature.

As an example, a workflow can implement one or more proximity metrics. For example, consider distance within a multi-dimensional space. As an example, distance may be along a coordinate axis or may be along coordinate axes. As an example, a distance may define a line, a triangle, a tetrahedron or other polygon in a multi-dimensional space. As an example, consider a three-dimensional space that utilizes 3D proximity in a (HI, $\Sigma$, $\rho_e$) space of a given mixture point to simulated values of the fluids of known composition for estimating fractions of these compounds in a reservoir fluid (see, e.g., the GUI 1210).

As an example, a workflow can enable treatment of a hydrocarbon phase for analyzing quantitatively reservoir fluid composition, using nuclear measurements, and generating a continuous composition log for an interval of interest. For example, consider the GUI 410 and the GUI 430 of FIG. 4. As an example, a workflow can output guidance for tool placement, for example, one or more operations. For example, consider guiding a tool in a downhole environment for sampling fluid and sampling fluid using the tool. Such a method may be implemented, for example, in a wireline fluid sampling operation.

As an example, a method can include performing phase behavior and PVT modeling of hydrocarbon mixtures and using one or more nuclear spatial distance techniques. As to PVT modeling, a method can include assessing performance of some examples of different EoSs. In such an example, an EoS as a model may be selected, for example, as to performance regarding densities of mixtures. Such an approach can include computing the composition of reservoir fluid. Such an approach can optionally include testing group examples to quality control various composition estimations, for example, with respect to one or more results from PVT composition analysis of downhole fluid samples. For example, consider a workflow that can optimize a sampling process by determining where samples are to be taken, how many samples to take, timing of samples, etc. For example, a workflow may be operatively coupled to a field operation where the field operation may be controlled using output of the workflow (e.g., intermediate output(s)) that can optimize the field operation.

As an example, a method can include characterizing phase behavior of a mixture. Characterizing can include defining the number of phases, phase volume fractions, phase compositions, and phase properties (molecular weight, density, and viscosity).

Calculation of phase behavior may be performed in one or more manners, for example, consider a "black-oil" manner or a "compositional" manner. As to a black-oil approach, it can be based on interpolation of PVT properties tables as a function of pressure and temperature, in which the oil and gas phase are considered as single components. As to a compositional approach, it can be based on a thermodynamically consistent model such as a cubic EoS.

An EoS can include semi-empirical relationships between pressure, volume and temperature of a pure substance. As an example, an EoS can be applied to mixtures with an additional variable (composition) and an appropriate mixing rule.

The validity of a black-oil PVT formulation tends to depend primarily on reservoir oil volatility. For example, if the reservoir fluid is a two-phase system at during production, then there will be some compositional effects, and applying a compositional model is more appropriate. The extrapolation of black-oil models to various reservoir fluids types tends to be inaccurate.

In a compositional model, known components can be utilized in an EOS to determine the number of phases present at one or more given pressures and temperatures. The uniformity of fugacity of each component, throughout various phases, as for chemical equilibrium, can be employed to determine equilibrium conditions regardless of the number of phases. As the effect of water on the hydrocarbon phase behavior can be neglected in various instances, phase equilibrium calculations may be focused on vapor-liquid equilibria. As an example, where there are both oil and gas phases, an approach can calculate the composition of each phase. Given these compositions, a method can then include calculating the co-existing phases' physical properties.

The process of determining how many phases are present is referred to as "flash". As the number and state of phases at equilibrium may not be known, solving phase equilibria with an EoS tends to be a trial-and-error procedure, in which the equilibrium ratio of each component phase fraction is estimated first and readjusted if the component fugacity equality is not respected. Such an approach can be computationally demanding.

As an example, a workflow can be a composition computation workflow. Such a workflow can include adding PVT compositional modeling capabilities to an inversion framework, which can provide improved results when compared to using a black-oil model approach. By defining and implementing a library of EoSs, a computational framework can provide for computing the phase equilibrium and the phases' density for various given hydrocarbon mixtures at reservoir pressure and temperature.

As an example, after the density of a fluid is computed, the fluid's components' mass fractions can be input to a forward modeling program that calculates the neutron slowing-down length, the thermal neutron diffusion length, the thermal neutron capture cross section, the hydrogen index, the electron density index, and one or more other nuclear parameters at the reservoir pressure and temperature for multiple hydrocarbon "types".

As an example, a workflow can include simultaneously solving, via a multiphysics inversion model, for the reservoir fluid mixture nuclear parameters. In such an example, the calculated parameters may be utilized in an inverse distance weighting (IDW) process to generate the composition of the reservoir fluid mixture. While IDW is mentioned, one or more other metrics may be utilized where, for example, such one or more metrics can include a distance or analog thereof that can be utilized in a multi-dimensional space (e.g., a nuclear parameter space).

As an example, a workflow can apply a technique that is a type of deterministic method for multivariate interpolation with a known scattered set of points. For example, given n nuclear parameters of a set of fluids of known composition, the spatial interpolation in a n-dimensional space can be used to compute the mass fraction values of each component of the reservoir fluid. Such an approach can scale a feature vector by the "amount of proximity" to the point to be solved, as it resorts to the inverse of the distance to each known point when assigning weights.

As an example, a workflow can consider log parameters such as electron density, hydrogen index and thermal neutron capture cross section (sigma, $\Sigma$). Such parameters can be referred to as nuclear parameters. As an example, a workflow can include utilizing at least two of such parameters where, for example, one of the parameters can be electron density ($\rho_e$).

Figure 6:
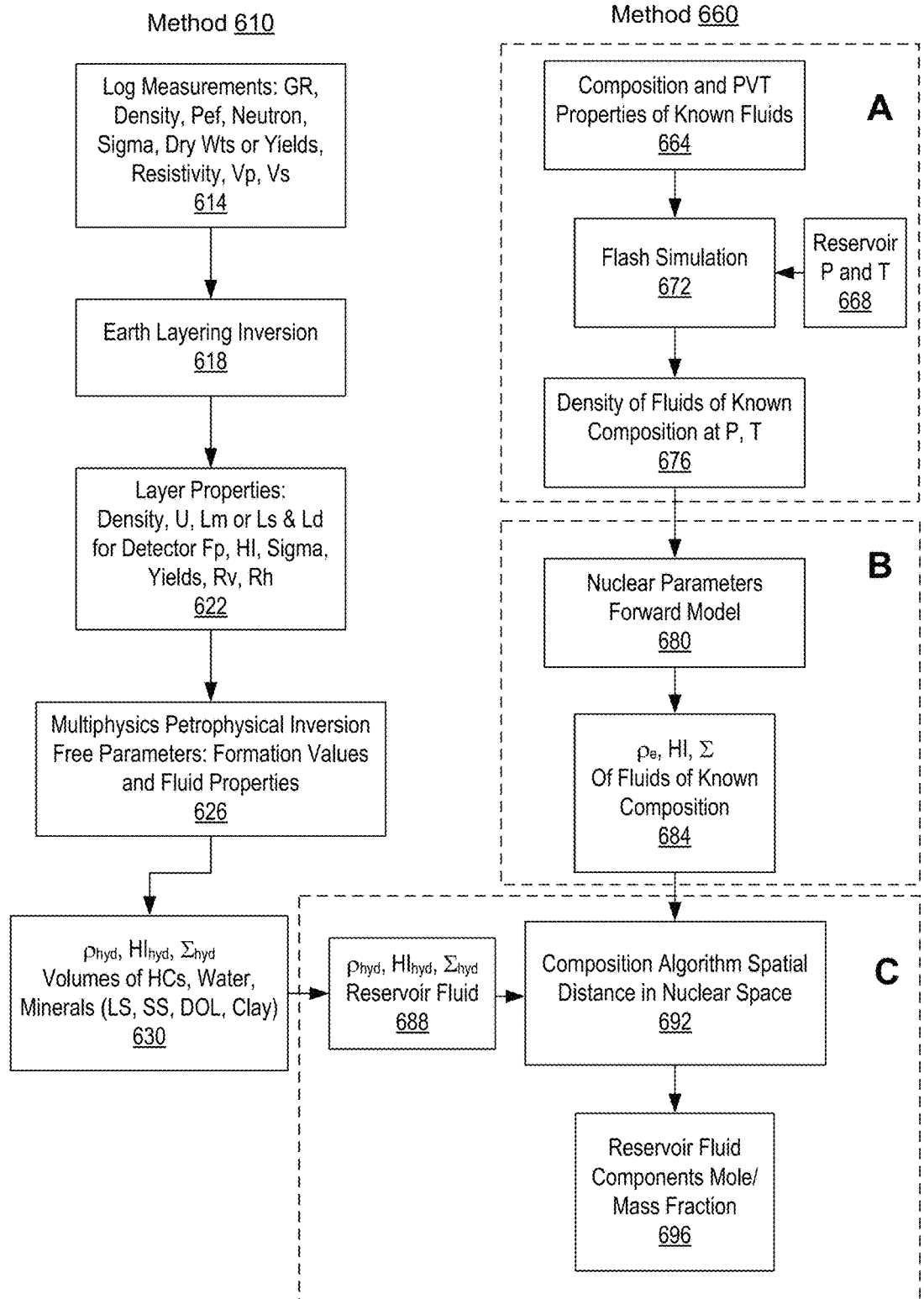
FIG. 6 illustrates an example of a method.

FIG. 6 shows an example of a method 600 that includes a method 610 and a method 660. As shown, the methods 610 and 660 can be operatively coupled where output of the method 610 is received as input to the method 660.

In FIG. 6, the method 610 includes a measurement block 614 for acquiring log measurements (e.g., GR, density, Pef, neutron, sigma, dry weights, yields, resistivity, Vp, Vs, etc.), an inversion block 618 for performing an earth layering inversion, a layer property block 622 for associating or determining properties for layers of a layer earth model (e.g., density, U, Lm or Ls and Ld for a detector Fp, HI, sigma, yields, Rv, Rh, etc.), and an inversion block 626 for performing a multiphysics petrophysical inversion for free parameters such as formation values and fluid properties. As shown, an output block 630 can output values from the inversion block 626, which can include density, hydrogen index and sigma, volumes of hydrocarbons, water and minerals (e.g., long-spacing (LS), short-spacing (SS), dolomite (DOL), clay, etc.).

As to the method 660, as shown in the example of FIG. 6, it includes a composition and properties block 664 for acquiring and/or generating composition and properties of known fluids, a reservoir pressure and temperature block 668 (e.g., for one or more reservoir pressures and/or one or more reservoir temperatures, as may be determining using sensor data, models, etc.), a simulation block 672 for performing a flash simulation, an output block 676 for outputting density of fluids of known composition at pressure and temperature as output of the simulation block 672, a forward modeling block 680 that utilizes the data of the output block 676 for performing forward modeling of nuclear parameters, an output block 684 for outputting electron density, hydrogen index and sigma as output of the forward modeling block 680, a reception block 688 for receiving output of the block 630 of the method 610 as input to the method 660 where the receiving includes receiving electron density, hydrogen index and sigma values for reservoir fluid, a spatial analysis block 692 for performing a composition algorithm spatial distance analysis in a defined nuclear parameter space using the received electron density, hydrogen index and sigma values for reservoir fluid and an output block 696 that outputs reservoir components mole fraction values and/or mass fraction values.

As an example, the output block 696 can be operatively coupled to one or more sets of executable instructions for one or more graphical user interfaces. In such an example, one or more graphical user interfaces can render composition data to a display, optionally in the form of a composition log. For example, consider the GUIs 410 and 430 of FIG. 4, which can be operatively coupled to the method 660 (e.g., optionally the methods 610 and 660).

In the example of FIG. 6, the method 610 can include utilizing a framework that includes one or more features of the TECHLOG framework (Schlumberger Limited, Houston, Tex.). For example, consider a three-dimensional petrophysical inversion engine (e.g., 3DP) that can be utilized for processing measurements from one or more downhole tools. For example, measurements acquired in a high-angle and/or horizontal well (HAHz) well can be used to define formation geometry around the well and populate layer properties. In such an example, one or more sources of geometrical models and/or remote bed boundary inversion maps may be used to enhance understanding of the formation geometry around the well. Such an approach can utilize a framework to interpret measurements, for example, to determine the position and properties of each layer that is traversed by the well.

As an example, the method 610 can be operatively coupled to a field operation or field operations. For example, the measurement block 614 can be part of a field operation that includes conveying one or more tools in a borehole or boreholes to acquire measurements. Such measurements, as indicated, may be subjected to multiphysics petrophysical inversion, which can output nuclear parameter values. Such values, as indicated, may be utilized to assess one or more fluids in a reservoir or reservoirs as subjected to the field operation or field operations.

Figure 7:
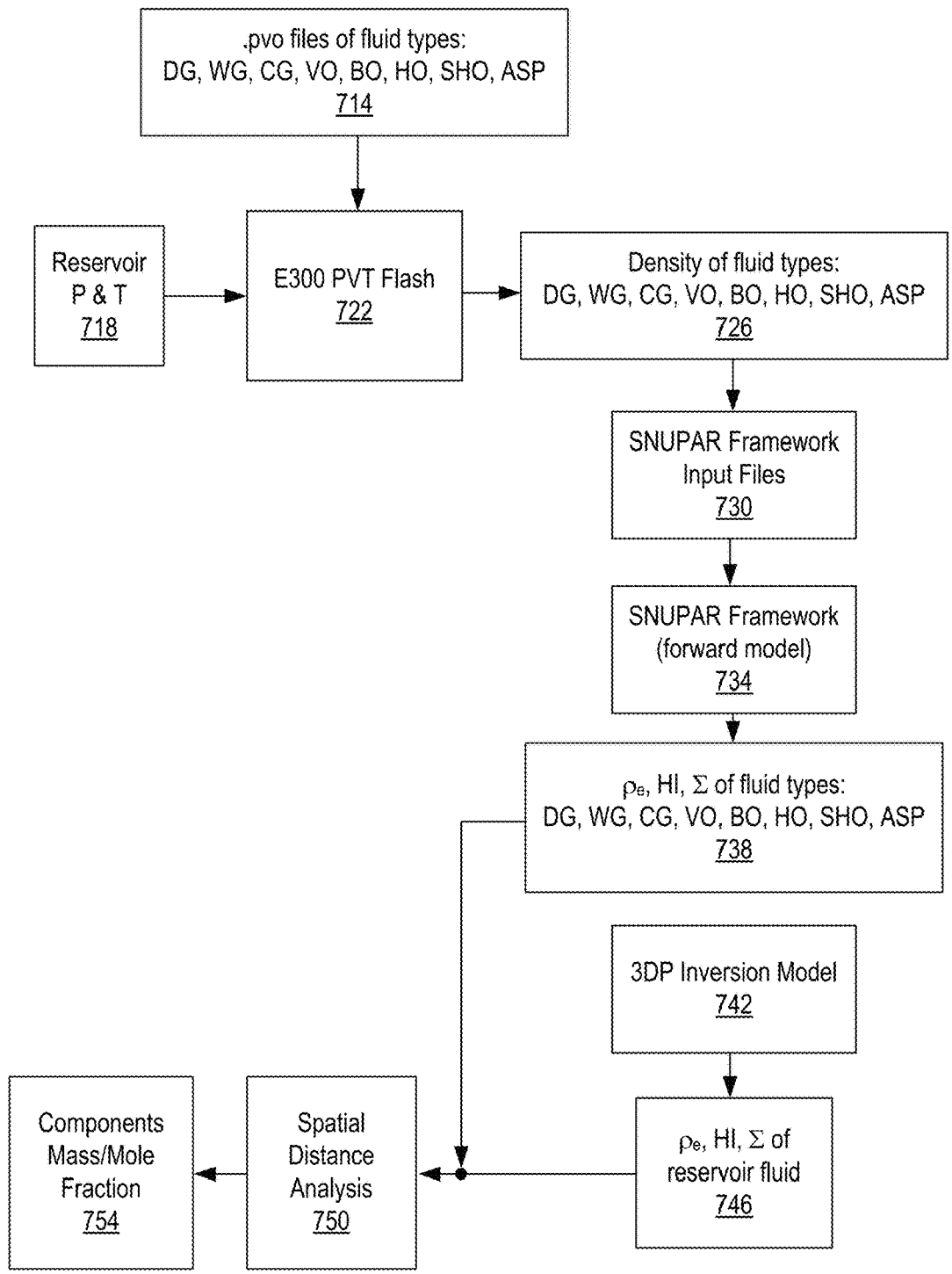
FIG. 7 illustrates an example of a method.

FIG. 7 shows an example of a method 700 that includes a fluid type file block 714 for providing files as to fluid type data for fluids of various types such as, for example, dry gas, wet gas, gas condensate, volatile oil, black-oil, heavy oil, super heavy oil, and asphaltene (e.g., DG, WG, CG, VO, BO, HO, SHO, ASP); a reservoir pressure and temperature block 718 for providing one or more pressures and/or one or more temperatures; a flash framework block 722 for performing flash computations that can utilize the E300 PVT flash framework; an output block 726 for outputting densities of fluid types as output of the flash framework block 722; a SNUPAR framework input file block 730 for providing input files suitable for input to the SNUPAR framework; a SNUPAR framework block 734 for performing computations to generate nuclear parameter values for fluid types; an output block 738 for outputting nuclear parameter values as output of the SNUPAR framework block 734, a 3DP inversion model block 742 for performing model-based inversions to generate nuclear parameter values as to reservoir fluid based on measurements; an output block 746 for outputting the generated nuclear parameter values as to reservoir fluid as output of the 3DP inversion model block 742; a spatial distance analysis block 750 that operates using the output of the block 738 and the output of the block 746; and an output block 754 for outputting components mass fraction values and/or mole fraction values according to the spatial distance analysis of the block 750.

As an example, the output block 754 can be operatively coupled to one or more sets of executable instructions for one or more graphical user interfaces. In such an example, one or more graphical user interfaces can render composition data to a display, optionally in the form of a composition log. For example, consider the GUIs 410 and 430 of FIG. 4, which can be operatively coupled to the method 700 (e.g., optionally one or more of the blocks 742, 746, 750 and 760). As an example, a GUI may provide for interactive control of one or more actions performed by one or more blocks of the method 700 (e.g., or the method 600). As an example, consider a slider control that can select a depth (e.g., measured depth) along a trajectory of a borehole to cause output of component information at the selected depth according to the block 754. As an example, such a slider may optionally control performance of a block such as the 3DP inversion model block 742 such that the inversion thereof is performed for a depth or depths that may be selected using a GUI (see, e.g., the GUIs of FIG. 4, etc.).

As an example, a system can include a database or databases with values of parameters sensitive to hydrocarbon composition for defined fluid types at various temperatures and pressures (see, e.g., the block 738). As an example, such a system can include a database or databases with values of parameters sensitive to hydrocarbon composition for reservoir fluid as associated with one or more boreholes (see, e.g., the block 746). In such a system, a user may utilize a computer to access the database(s) and perform a spatial distance analysis as in the analysis block 750 to generate components mass fraction and/or mole fraction as in the output block 754. In such an approach, the user may select a number of different types of fluids (e.g., two or more of DG, WG, CG, VO, BO, HO, SHO and ASP, etc.) and a corresponding number of clusters to perform a spatial distance analysis in a multidimensional parameter space. Such an approach can include selecting a multivariate interpolation technique, which may be, for example, a type of an inverse distance weighting (IDW). IDW is a type of deterministic method for multivariate interpolation with a known scattered set of points such as, for example, parameter values in a multi-parameter space, where, for example, assigned values to unknown points may be calculated with a weighted average of the values available at the known points. Such a technique can utilize an inverse of the distance to each known point ("amount of proximity") when assigning weights.

As to a database or databases supplying values of the block 746, as an alternative or additionally, one or more values may be supplied via the 3DP inversion model block 742 in substantially real-time (e.g., near real-time) from measurements acquired using a downhole tool disposed in a borehole. In such an approach, the output block 754 may be utilized to generate a substantially real-time composition log (e.g., compositional log) for positions of the downhole tool (e.g., as the downhole tool is conveyed in the borehole, etc.).

In the example of FIG. 7, the flash computations of the block 722 tend to be computationally intensive. By selecting a particular number of fluid types (e.g., DG, WG, CG, VO, BO, HO, SHO and ASP, etc.), the number of flash computations can be controlled. As an example, the flash computations of the block 722 may be performed at least in part in parallel using parallel processing technology (e.g., multiple cores, multiple threads, virtual machines, etc.). As an example, for clustering, a number of clusters may be selected based on a number of fluid types for which flash computations have been performed. For example, if the number of fluid types is eight, then the number of clusters may be selected to be eight, or optionally less. In such an approach, a user that interacts with a system via a GUI to perform the spatial distance analysis as in the analysis block 750, may select a number of fluid types to correspond to a number of clusters. As explained, through use of fluid types, the number of flash computations can be controlled; noting that selection of temperatures and pressures may be in a range that can be expected for a particular field (e.g., a basin, a reservoir, etc.) under development, production, etc. A fluid type approach can reduce flash computations demand when compared to a fluid pure component approach. For example, a number of components may be many whereas a number of fluid types may be an order of magnitude less (or more than an order of magnitude less). As explained, a fluid type approach can carry over and reduce computational demands as to analysis such as a spatial distance analysis as clustering can be performed for fluid type clusters.

As to pressures and temperatures for purposes of analysis, a downhole tool can include one or more pressure sensors and/or one or more temperature sensors. Such sensor or sensors can acquire measurements where such measurements may be utilized to compute and/or select parameter values of fluid types (see, e.g., block 738). As an example, additionally or alternatively, pressure and/or temperature may be determined by inverting other measurements (e.g., sigma, NMR T1, diffusion coefficient, density, etc.). For example, consider one or more techniques as described in WO2017074884A1, published 4 May 2017, entitled Formation Evaluation, which is incorporated by reference herein. In such an approach, an inverted temperature and/or an inverted pressure may optionally be utilized for computing and/or selecting parameter values of fluid types and/or for comparison to measurements of temperature and/or pressure.

As an example, the analysis block 750 can include utilizing a power parameter as part of a spatial distance analysis. For example, a power parameter can control effect of distance where a larger value of the power parameter acts to diminish the influence of "distant" points in a multidimensional parameter space (e.g., nuclear parameter space) and where a smaller value of the power parameter acts to increase the influence of "distant" points in a multidimensional parameter space (e.g., nuclear parameter space). As an example, a method can include selecting a power parameter value that is greater than unity to reduce influence of points as they become more distant with respect to a reference point. As an example, the analysis block 750 can include selecting a domain within a space that excludes various points, which may be considered distant from an expected region of interest in the space (e.g., a span or spectrum of particular fluid types).

Figure 8:
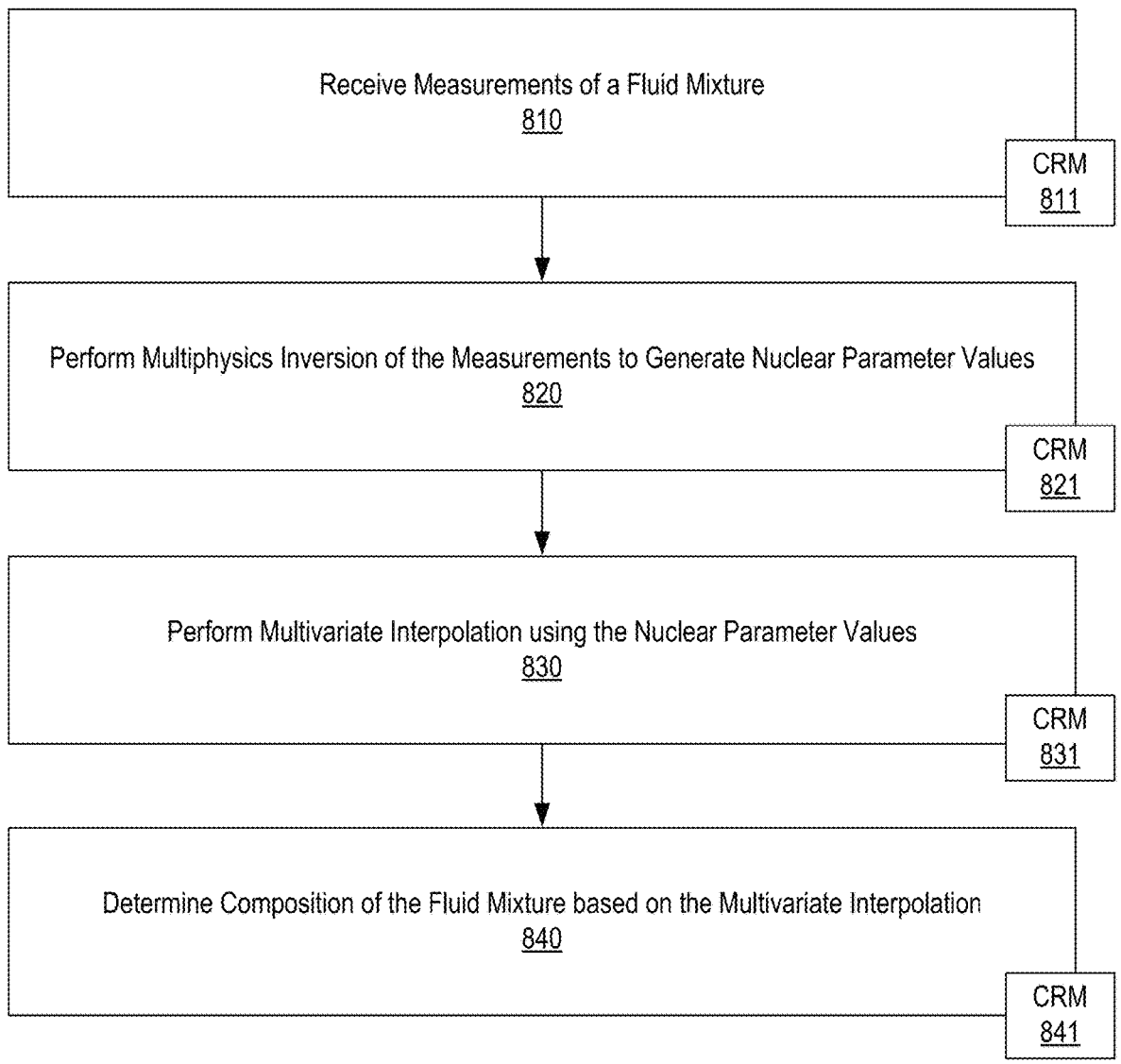
FIG. 8 illustrates an example of a method.

FIG. 8 shows an example of a method 800 that includes a reception block 810 for receiving measurements of a fluid mixture where the measurements are acquired by at least one downhole tool; a performance block 820 for performing a multiphysics inversion of the measurements to generate nuclear parameter values for the fluid mixture; a performance block 830 for performing a multivariate interpolation using the generated nuclear parameter values that accounts for intermolecular interactions in the fluid mixture; and a determination block 840 for determining a composition of the fluid mixture based on the multivariate interpolation.

The method 800 shows various computer-readable media (CRM) blocks 811, 821, 831 and 841 (e.g., non-transitory media that are not carrier waves and that are not signals). Such blocks generally include instructions suitable for execution by one or more processors (or cores) to instruct a computing device or system to perform one or more actions. As an example, a single medium may be configured with instructions to allow for, at least in part, performance of various actions of the method 800 of FIG. 8.

As an example, the method 800 can include nuclear parameter forward modeling such as in the method 660 (see, e.g., the block 680 of the method 660 or the block 734 of the method 700) to generate nuclear parameter values (e.g., for electron density, HI and sigma) as to fluid mixtures of known compositions. As an example, the method 800 can include performing a flash simulation (see, e.g., the block 672 of the method 660 or the block 722 of the method 700), which may be performed prior to nuclear parameter forward modeling.

As an example, the method 800 can include estimating composition using spatial interpolation such as, for example, inverse distance weighting (IDW), which is a type of multivariate interpolation. IDW can provide operate such that an expected result is a discrete assignment of an unknown function concentration $c_j$, for a component j, in a study region. An IDW interpolation can explicitly assume that things that are close to one another are more alike than those that are farther apart. To predict a value for a selected unmeasured location, IDW can use the measured values surrounding the prediction location where measured values closest to the prediction location have more influence on the predicted value than those farther away.

As an example, a method can include receiving reservoir fluid properties; clustering using a selected "k" value; assigning fluid types to clusters; and outputting the assigned clusters, for example, to a GUI. In such an example, a loop can be included such that a "k" value may be selected, for example, to alter output. For example, a method can include increasing the k value if it is deemed too low (e.g., spatially large cluster(s)) or decreasing the k value if it is deemed too high (e.g., spatially small cluster(s)). As an example, a GUI can include a graphical control that can allow a user to select, de-select, adjust, etc., a cluster, a k value, etc.

Figure 9:
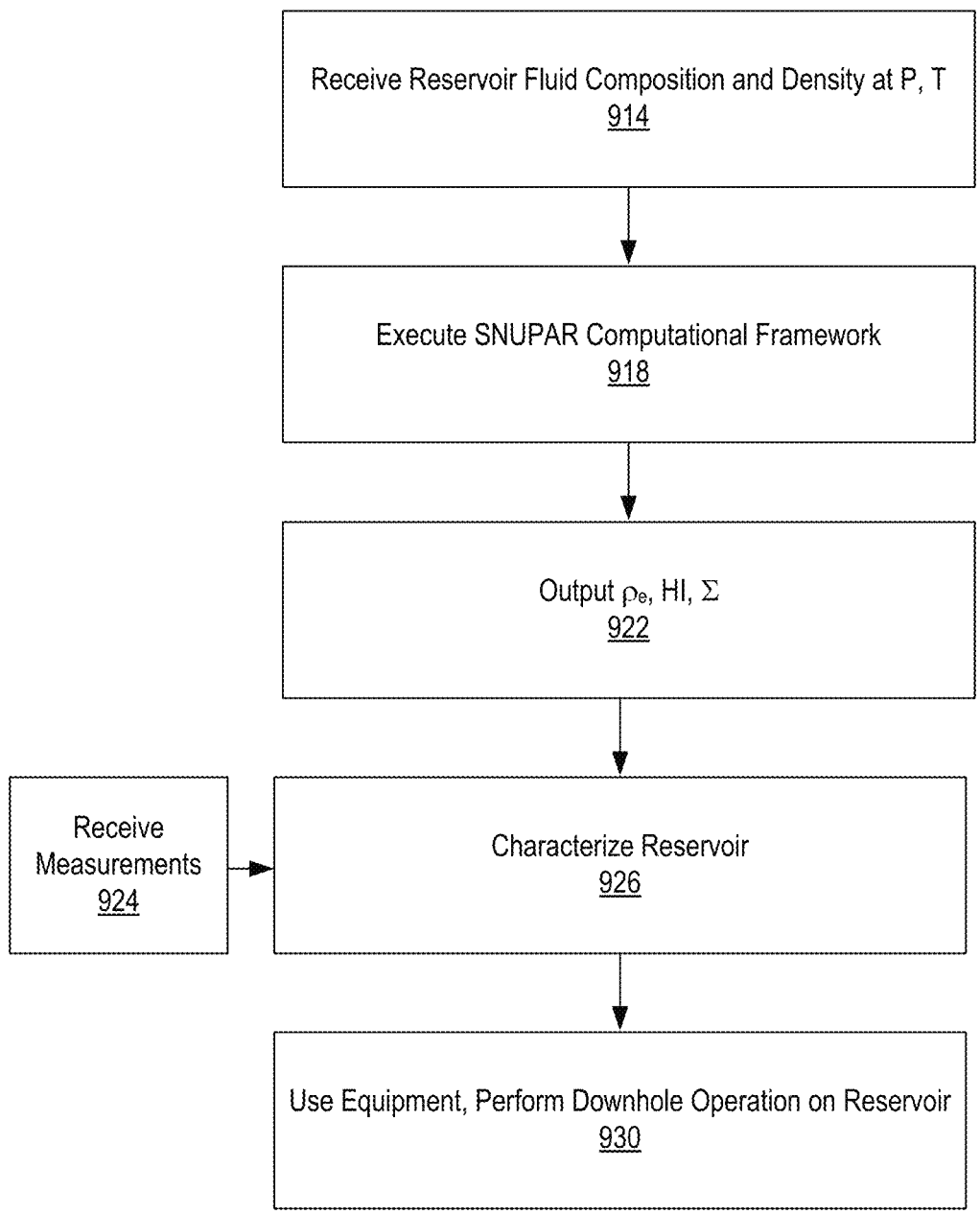
FIG. 9 illustrates an example of a method.

FIG. 9 shows an example of a method 910 that includes a reception block 914 for receiving reservoir fluid composition and density data for one or more pressures and/or one or more temperatures; an execution block 918 for executing a SNUPAR computational framework; an output block 922 for outputting nuclear parameter values (e.g., at the pressure(s) and temperature(s)); a reception block 924 for receiving reservoir measurement; a characterizing block 926 for charactering a reservoir using the output of the output block 922 and the measurements of the reception block 924; and a performance block 930 for performing one or more downhole operations on the reservoir using equipment. In the example of FIG. 9, the block 926 can include performing a 3DP inversion, for example, such as in the block 742 of the method 700 of FIG. 7. In the example of FIG. 9, the block 926 can include performing a spatial distance analysis, for example, such as in the block 750 of the method 700 of FIG. 7.

As an example, a method can include PVT modeling using a C++ computer code application programming interface (API), a PVT framework with libraries of component properties, correlations for characterization of C30+ components and two-phase P-T flash calculations.

In an example trial, each fluid tested was constructed using the mass/molar composition of gas chromatography results from downhole samples taken from several fields throughout the world. The PVT library included the following properties of the components: molecular weight; critical pressure; critical temperature; critical molar volume; critical Z-factor; acentric factor; and parachor.

Such properties along with each component mass fraction and the Binary Interaction Coefficients for each component pair can be defined in an input file that is used by a flash simulator engine of a flash framework. In such an approach, a two-phase flash calculation can include defining amounts and compositions of equilibrium phases, given pressure, temperature, and mixture composition. In such an approach, the mixture may exist as a single phase or may split into two or more phases. In such an approach, phase equilibria in a liquid-vapor system can be calculated with an EoS by satisfying the condition of chemical equilibrium, in which the chemical potential of each component in the liquid phase is to be approximately equal to the one in the vapor phase.

Various example EoSs, (see, e.g., PR, SRK, SRK-P, etc.) can be selected for assessment. As volumetric behavior in petroleum engineering applications tends to implement the Peng-Robinson (PR) derived EOS, or a modification of the Soave-Redlich-Kwong (SRK) EoS, these two EoSs selected. Both, cubic EoSs, can be expressed in terms of the compressibility factor $Z=pv/RT$, $$Z^3 + A_2 Z^2 + A_1 Z^1 + A_0 = 0$$

where constants $A_0$, $A_1$, and $A_2$, functions of pressure, temperature, and phase composition, differ for both EoSs. In both equations, the constants may be rearranged and expressed as function of van der Waals' attraction and repulsive parameters, being therefore 2-parameters equations.

The Peng Robinson equation can be modified to adjust the function of the acentric factor, as recommended for heavier components. An adjustment to both SRK and PR two-parameters EoS can be that proposed by Peneloux et al., introducing a third constant, c, without changing the equilibrium calculations of the original two-constant equation. The volume-translation constant c solves the deficiency of two-constant EOS in liquid volumetric predictions.

As an example, an adjustment term can be applied to the EoS-calculated molar volume, $v=v_{EOS}+c$, where v is adjusted molar volume, $v_{EOS}$ is the two-parameter EoS calculated volume, and c is a component-specific constant.

As an example, consider selecting one or more of: PR2: Two-parameter Peng-Robinson (1976); PR2_C: Two-parameter Peng-Robinson adjusted (1978); PR3: Three-parameter Peng-Robinson (1976) [with Peneloux (1982) adjustment]; PR3_C: Three-parameter Peng-Robinson adjusted (1978) [with Peneloux (1982) adjustment]; SRK2: Two-parameter Soave-Redlich-Kwong (1972); SRK3: Three-parameter Soave-Redlich-Kwong (1972) [with Peneloux (1982) adjustment].

The two-phase flash simulator implemented returns the liquid and vapor volume fraction and mass densities, which are then combined to output the fluid's bulk density.

Flash results of the above list of EoSs for several fluid samples were compared against results from constant composition expansion experiments (CCE) conducted in a laboratory.

For an oil sample, a CCE experiment determined the bubble-point pressure, under saturated-oil density, isothermal oil compressibility, and two-phase volumetric behavior at pressures below the bubble-point. The procedure for the CCE experiment starts with filling a cell with a known mass of reservoir fluid. Reservoir temperature can be set to be held constant during the experiment. The sample initially is brought to a condition somewhat above initial reservoir pressure, ensuring that the fluid is single phase. As the pressure is lowered, oil volume expands and is recorded.

Results from a trial for a gas condensate reservoir sample at 86 degrees C. (187 degrees F.) were generated. In this example both three-parameter Peng Robinson equations yielded superior results, for example, with 3.83 kg/m³ root-mean-square error (RMSE) or total standard error of the estimate for 14 data points. RMSE is a measure of accuracy, to compare forecasting errors of different models for a variable, being defined as:

$$RMSE = \sqrt{\frac{\Sigma_i^n (\rho_{lab,i} - \rho_{estimated,i})^2}{n}}$$

Representing the sample standard deviation of the differences between predicted values and observed values, RMSE serves to aggregate the magnitudes of the errors in predictions into a single measure of predictive power.

An EoS may be selected using results, for example, a representation of the combined standard error of estimate for a total of 172 pressure and temperature data points, using 15 fluid samples and 6 EoSs, making a total of 1072 flash simulations.

Combining data from different fluids together in a single total RMSE, a similar performance between three-parameter EOS, SRK3, PR3 and PR3_C, with SRK3 was observed outputting a combined error of 26.7 kg/m³.

As mentioned, a workflow can include a reservoir fluids database clustering analysis that can classify data into fluid types. As an example, EoS-predicted downhole mixture density at the formation pressure and temperature for fluid types can be used in a nuclear forward modeling program that converts the mixture composition and mixture density to nuclear parameters of interest, electron density index ($\rho_e$), hydrogen index (HI), and thermal neutron capture cross section ($\Sigma$).

To quality control the ability to predict fluid compositions from the EoS- and program-computed reservoir fluid properties from logs, more than 514 reservoir fluid samples were provided by a laboratory.

Figure 11:
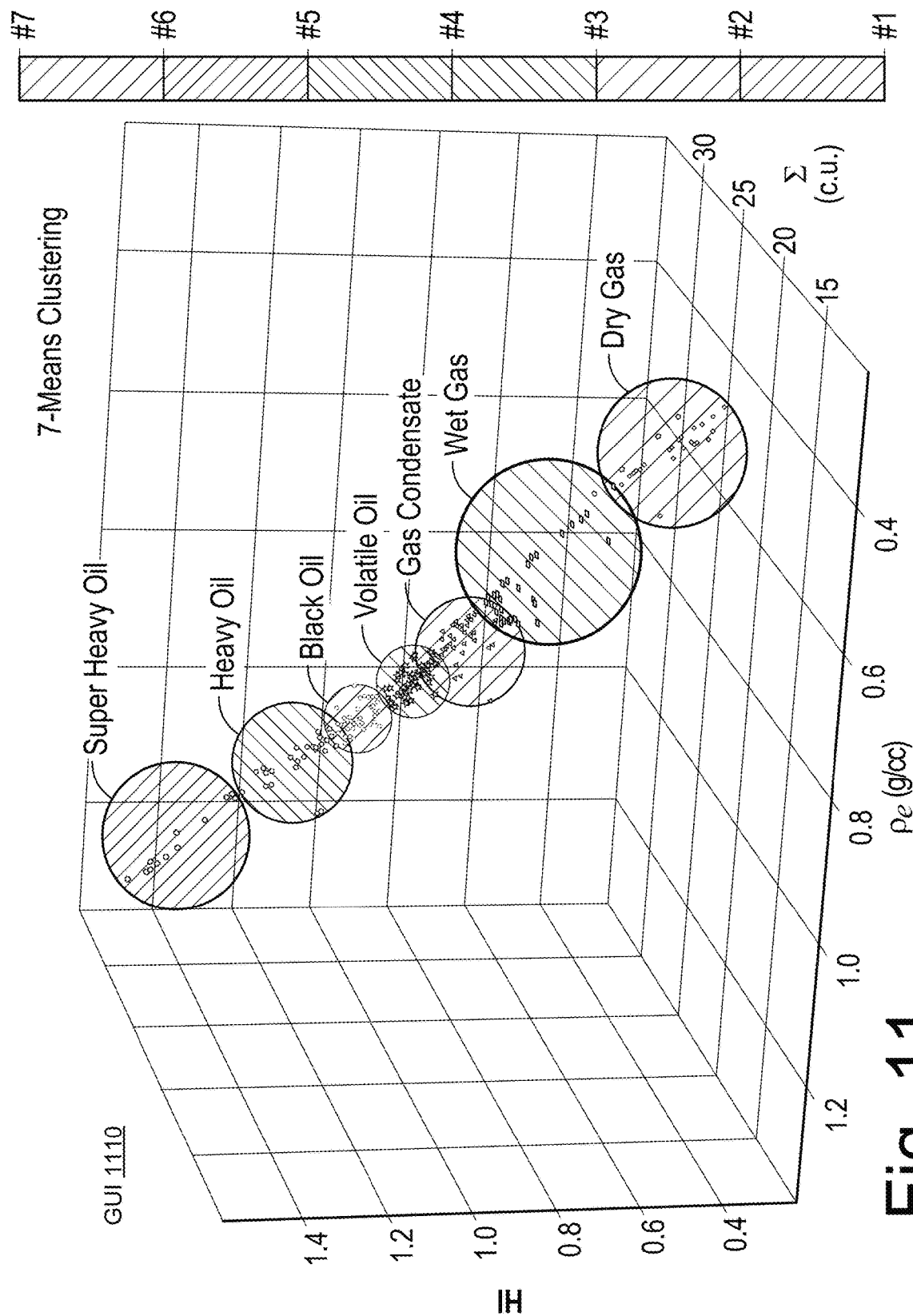
FIG. 11 illustrates an example of a graphical user interface.
Figure 12:
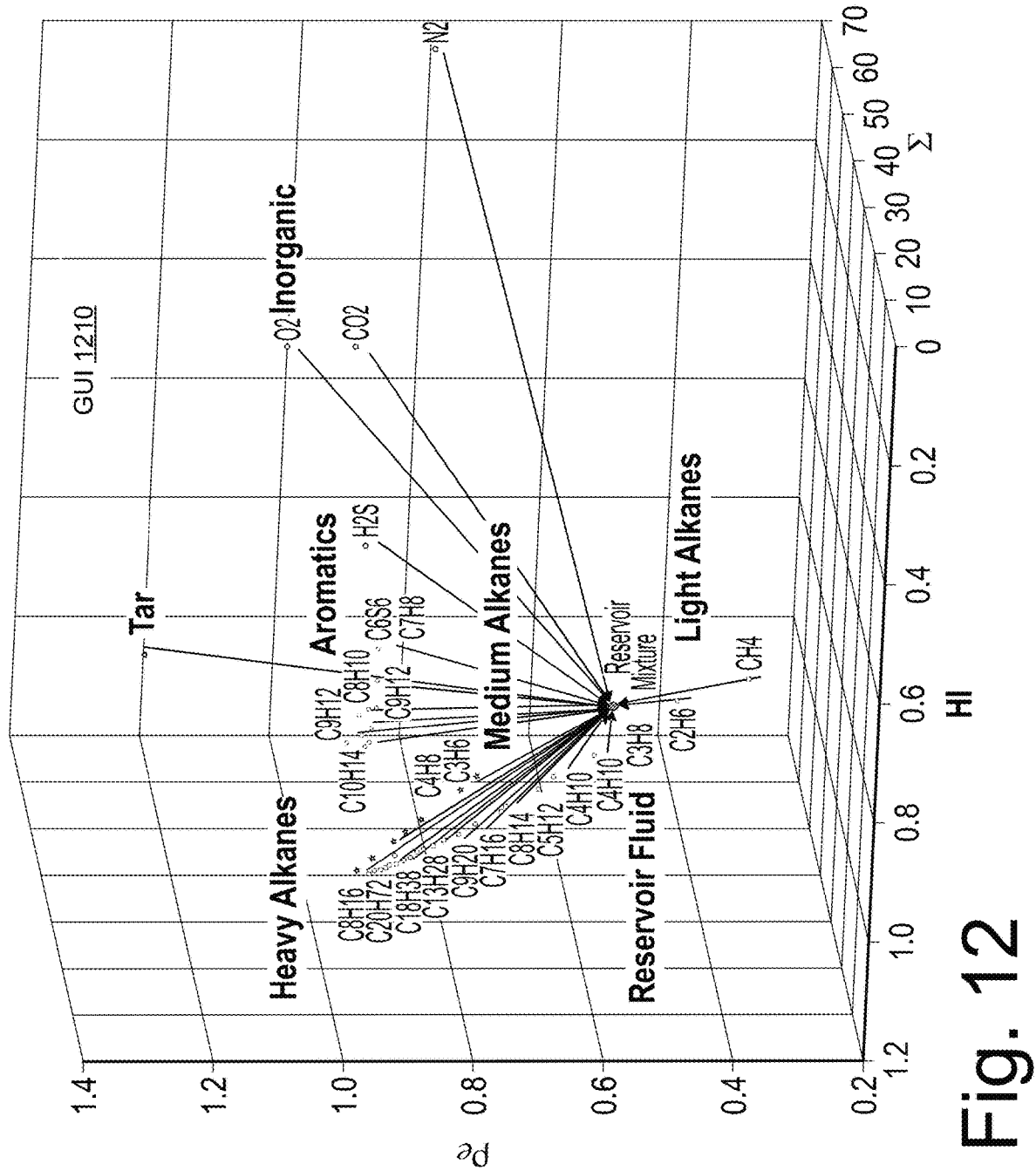
FIG. 12 illustrates an example of a graphical user interface.
Figure 13:
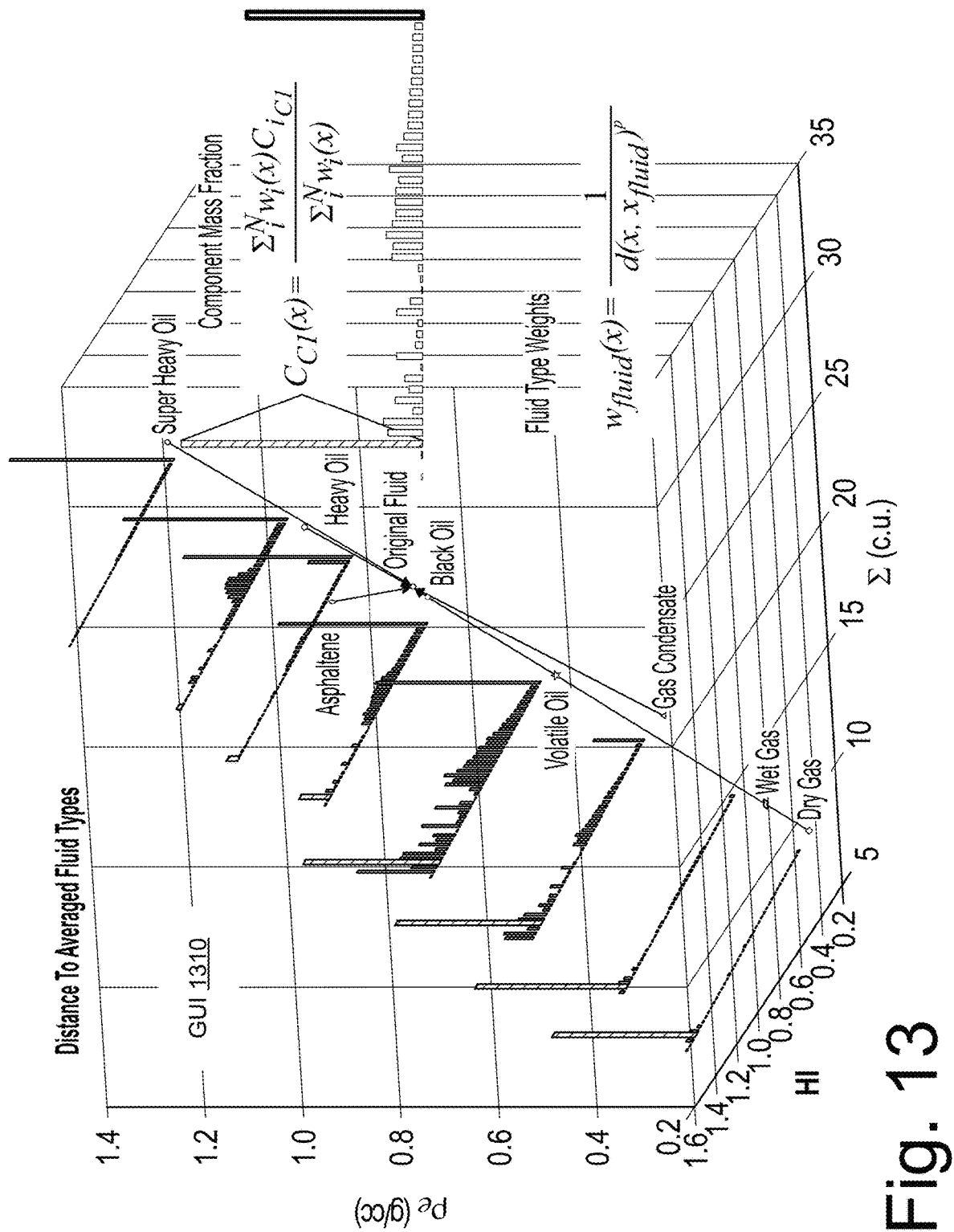
FIG. 13 illustrates an example of a graphical user interface.
Figure 14:
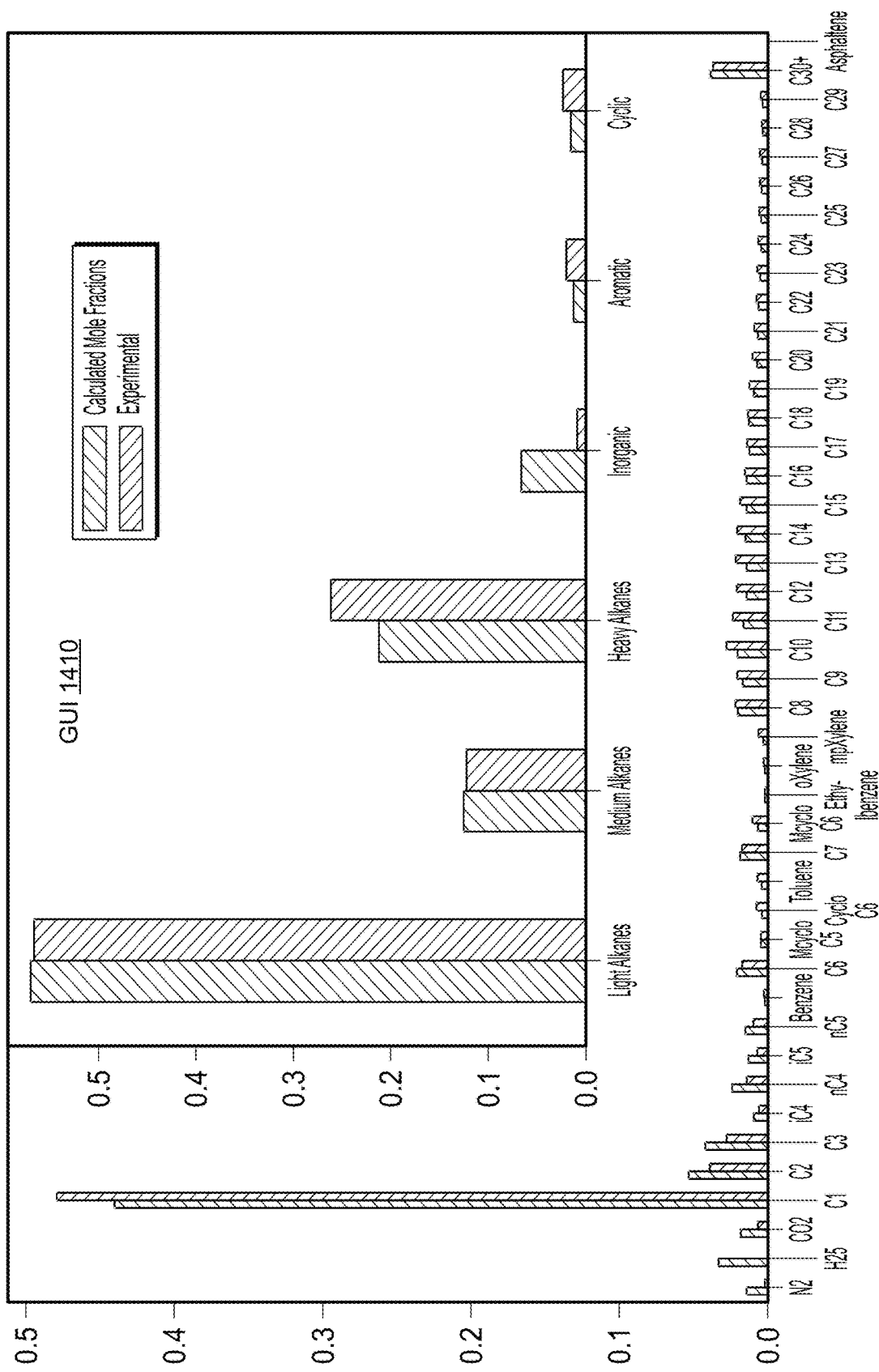
FIG. 14 illustrates an example of a graphical user interface.

FIGS. 10, 11, 12, 13 and 14 pertain to various examples of approaches that can be utilized for processing data such as laboratory data (e.g., as may be in a database or databases) to generate suitable fluid types, which may be via clustering in a multi-nuclear parameter space (see, e.g., FIG. 11), as well as for processing measurements as acquired downhole, which can include utilizing a spatial distance analysis. As explained, for example, with respect to FIG. 13, points in a multi-nuclear parameter space can each represent a fluid type with an associated distribution (e.g., component mass fraction). Such an approach can be utilized, for example, to characterize reservoir fluid. As to FIG. 12, it shows distances to pure components; whereas, FIG. 13 shows distances to averaged fluid types. FIG. 14 shows some examples of comparisons between computed values for fractions and experimental values (e.g., laboratory values). As explained, nuclear parameter values for fluid types defined in a multi-nuclear parameter space may be utilized for performing a spatial distance analysis of nuclear parameter values for reservoir fluid (see, e.g., the blocks 738, 746, 750 and 754 of FIG. 7). Output from such an approach may be in one or more forms (e.g., a composition log, a plot, a multi-dimensional plot, a combination of plots and logs, etc.). As explained, a multiphysics inversion technique can be implemented to invert for downhole reservoir fluid properties of electron density, HI, and sigma using downhole tool measurements where a spatial distance analysis can be utilized to then estimate mass fractions of hydrocarbon components of the reservoir fluid via spatial distance calculations of the inverted properties with respect to fluid types' EoS derived properties. Such an approach may be utilized to generate a continuous composition log for an interval of interest along a borehole.

Figure 10:
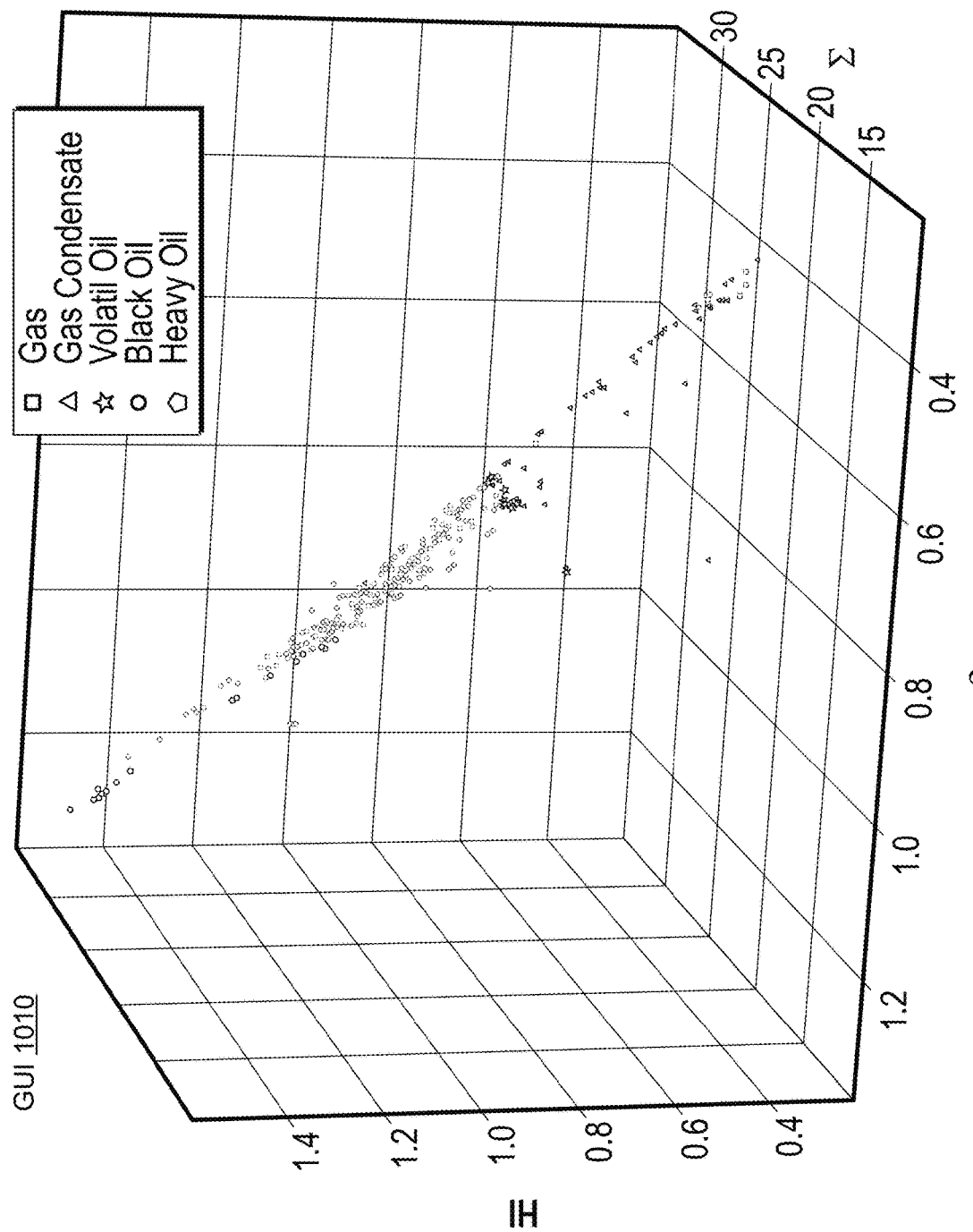
FIG. 10 illustrates an example of a graphical user interface.

FIG. 10 shows an example of a graphical user interface (GUI) 1010 that shows computed properties of values in a fluids' database at a given pressure and temperature. The samples were classified in accordance to their composition and volumetric behavior at the reservoir and surface conditions, and labeled as gas (G), gas condensate (GC), volatile oil (VO), black oil (BO) and heavy oil (HO). Those samples were then clustered and averaged according to their components distribution. The resulting fluids were named as fluid types in a workflow. In the GUI 1010, the calculated fluids' nuclear proprieties for entries in the database at 7,000 psi (e.g., 48 MPa) and 170 degrees F. (e.g., 77 degrees C.).

In such an approach, certain clusters tended to have much larger sample size than others and a very dispersed distribution in proportion to the fraction of light, medium and heavy alkanes. Thus, to improve the data set separation, a k-means clustering technique was implemented to divide the dataset into k partitions (clusters), which were selectively fixed a priori. Such an approach aims to partition n observations into k clusters in which each observation belongs to the cluster with the nearest mean. Such an approach uses Euclidean distance used as metric and variance is used as a measure of cluster scatter. Because the number of clusters k is an input parameter, an inappropriate choice of k may yield sub-optimal results.

As an example, a workflow included adjusting the number of clusters (e.g., k value), for example, a workflow first split data into five clusters that followed a laboratory labeling convention. Besides the dependence to the value k selected, another factor can be the selected cluster model itself, which may be, for example, based on spherical clusters, separated so that the mean value converges towards the cluster center. In this model, the clusters are expected to be of similar size, so that the assignment to the nearest cluster center is the appropriate assignment.

As mentioned, a method can include optimizing a number of clusters. As an example, a number of clusters may be in some instances a secondary concern to defining a set of cluster centroids that cover a desirable spectrum of hydrocarbon composition. As an example, a method can include assessing a spectrum of hydrocarbon compositions represented by clusters and adjusting one or more clustering parameters to increase, decrease, focus, etc., a span of clusters in a multidimensional space. As an example, a method can include setting one or more limits with respect to one or more coordinate axes of nuclear parameters as part of a clustering process.

FIG. 11 shows an example of a graphical user interface (GUI) 1110 that includes a three-dimensional nuclear parameter space for electron density, hydrogen index and sigma with seven clusters (DG, WG, GC, VO, BO, HO and SHO), which correspond to a clustering process with a k value of seven. As shown, the clusters span a substantially linear path within the multidimensional space over a range of electron density values (e.g., 0.4 to 1.4 g/cc), a range of hydrogen index values (e.g., 0.2 to 1.6) and sigma values (e.g., 10 to 35 c.u.). The GUI 1110 includes a scale with seven regions with hash marks that indicate the seven clusters. As shown in the example GUI 1110, the clusters differ in size where the wet gas cluster is the largest and the black oil cluster the smallest. As an example, a method can include generating cluster size metrics and ordering clusters with respect to size. Such an approach may be utilized in assessing clusters and optionally optimizing clusters, for example, to decide whether a small cluster can be merged (e.g., into one or more other clusters) and/or a large cluster split (e.g., refined to multiple clusters, etc.). As an example, a clustering process can be iterative and utilize one or more pre-defined labels as to fluid type where the labels may be hierarchical. For example, wet gas may be a label for different types of wet gas where a process may optionally resolve a large wet gas cluster into two or more different types of wet gas. As another example, consider super heavy oil being a label for different types of super heavy oil where a super heavy oil cluster may be resolved into two or more different types of super heavy oil. As an example, a resolution process may include selecting a cluster and increasing a k value where the k value may be a local k value for the selected cluster. In such an example, an initial process may utilize a k value of 6 over a span in a multidimensional space and then select a cluster and set a k value to 2 or more for that cluster over a span associated with that cluster in the multidimensional space.

As mentioned, a process can include averaging resulting groups according to their composition and labeling with respect to type of fluid such as, for example, dry gas, wet gas, gas condensate, volatile oil, black oil, heavy oil and super heavy oil. As an example, consider a process that adds an additional black oil fluid sample including approximately 50 percent mass fraction of asphaltenes, which may be selected for a fluid types set and labeled as asphaltene-rich oil (ARO).

As an example, a workflow can include computing hydrocarbon component mass fraction values. A method can include solving a problem of estimating hydrocarbon composition of a mixture by using spatial interpolation between points of pure compounds and the mixture.

FIG. 12 shows an example of a graphical user interface (GUI) 1210 that includes various distance metrics in a multidimensional nuclear parameter space. Specifically, the GUI 1210 shows computed nuclear responses for pure components and reservoir fluid and a number of distances for defining the reservoir fluid.

In the GUI 1210, the distance metrics are shown with respect to points that represent different types of hydrocarbons as well as a reservoir fluid point (see "Reservoir Mixture"). As shown, labels can be defined and rendered such as light alkanes, medium alkanes, heavy alkanes, tar and inorganic (e.g., $N_2$, $O_2$ and $CO_2$). As shown, the multidimensional nuclear parameter space can be defined with axes that span a sufficient range to include one or more desired types of components to be included in an analysis as to reservoir fluid (e.g., consider a composition log analysis that generates a composition log or logs). As an example, a method can include adjusting an axis, switching axes, etc. As an example, a method can include making an axis linear, non-linear, logarithmic, etc. In such an approach, a spatial resolution may be adjusted with respect to one or more nuclear parameters.

In the example GUI 1210, distances are determined and rendered as being between the reservoir fluid point and various components (e.g., rather than using a number of lesser fluid types). As an example, a method can include fitting a curve for hydrocarbons' major groups; however, such an approach may be sub-optimal in various instances where inter-molecular interactions in a mixture exist that may lead to inaccuracies. As an example, a method can include considering the effect of inter-molecular interactions in a mixture density and therefore in its nuclear response. For example, rather than calculating the nuclear response of each pure component at reservoir pressure and temperature, the density of each averaged fluid type cluster, computed by a flash simulator, can be input to a nuclear parameters computation framework along with the fluid types' composition. As explained, such an approach can reduce flash computation demands.

FIG. 13 shows an example of a GUI 1310 that includes a multidimensional nuclear parameter space with various data graphics as to composition of types of fluids along with distance metrics. Specifically, each type of fluid includes its own composition spectrum that includes a series of component mass fraction values. As an example, a method can include characterizing a reservoir fluid using a plot or plots such as one or more of those in the GUI 1310.

In the example of FIG. 13, a user may readily visualize the constituents of each of the types of fluids and the composition thereof in terms of mass fraction (e.g., or mole fraction, etc.). As an example, a clustering process may optionally include assessing such composition data and determining whether to adjust a k value or other clustering parameter based on such composition data. For example, where a multimodal distribution exists for a type of fluid, the multimodal distribution may optionally be subjected to splitting and optionally merging with one or more other types of fluids. In the example of FIG. 13, the simulated HI, $\Sigma$, and $\rho_e$ values from the fluid types can be then compared against solved reservoir fluid values from a multiphysics inversion model, for example, to generate graphics as in the GUI 1310 for a reservoir fluid. As an example, a method may include using inverse distance weighting as a multivariate interpolation and using a k-Nearest Neighbors (k-NN) technique.

As an example, a workflow can include applying a technique such as inverse distance weighting (IDW), which states that the expected result is a discrete assignment of the unknown function concentration $c_j$, for a component j, in a study region:

$$c_j(x): x \to \mathbb{R}, x \in D \subset \mathbb{R}^n,$$

where D is the study region.

The IDW interpolation explicitly assumes that items that are close to one another are more alike than those that are farther apart. To predict a value for any unmeasured location, IDW uses the measured values surrounding the prediction location. The measured values closest to the prediction location can have more influence on the predicted value than those farther away.

As an example, consider an approach that calculates the 2-norm of the distance vector from the mixture data point to each fluid type. In such an approach, the 2-norm is the usual Euclidean length, defined in the three-dimensional Euclidean space R3 as:

$$d(x, x_i) = \|d\|_2 = \left(\sum_{n=1}^{3} |d_n|^2\right)^{\frac{1}{2}}$$

A general form of finding an interpolated value $c_j$ at a given point x based on samples $c_{1_j} = c(x_1)$ for i=1, 2, ... N is:

$$c_j(x) = \begin{cases} \dfrac{\sum_{i=1}^{N} w_i(x) c_{i_j}}{\sum_{i=1}^{N} w_i(x)} & \text{if } d(x, x_i) \neq 0 \\ c_i & \text{if } d(x, x_i) = 0 \end{cases}$$

where $$w_i(x) = \frac{1}{d(x, x_i)^p}$$

is the weighting function, that inverts the distances to fluid types, p is a positive number, called power parameter, and N is the total number of fluid points used. The weight decreases as distance increases from the interpolated points. Greater values of $\rho$ assign greater influence to values closest to the interpolated point. As an example, consider setting the power parameter to a value of unity; noting that one or more other values may be utilized as part of a workflow.

As an example, the mass concentration function c can be characterized as mentioned for each pure component j, representing the sum of the contribution from each fluid type considered. A workflow can include processing such that the obtained values for each component j are normalized, for example, to reduce truncation error.

$$C_{j\,norm} = \frac{c_j}{\sum_{j=1}^{ncomp} c_j}$$

A modification to the foregoing approach can include calculating an interpolated value using the k-nearest neighbors (k-NN) instead of the full sample. The modified approach can be defined as follows: Compute the Euclidean distance from the query point to the mixture points; Order the labeled mixtures by increasing distance; Find a heuristically optimal number k of nearest neighbors, based on RMSE; and Calculate an inverse distance weighted average with the k-nearest multivariate mixture neighbors.

As an example, a method that includes clustering and use of fluid types can be computationally efficient. For example, when compared to an approach that utilizes pure components, the fluid types approach can reduce the number of computations as may be utilized in a multivariate interpolation such as the inverse distance weighting approach. Through a reduction in computations, a system or tool can be made more efficient, which may allow for real-time determinations of composition of fluid mixtures (e.g., reservoir fluid, which are known to be mixtures of various components that include one or more hydrocarbons). As an example, a number of clusters or fluid types may be a factor that is adjustable depending on desired computational efficiency. For example, fewer fluid types may provide for greater efficiency (e.g., computational speed, implementation using fewer computational resources, etc.).

As an example, a method can include excluding the most distant mixture points, which may be part of an optimization process (e.g., to determine an optimum global or local k value). As an example, a method can include making one or more adjustments to a power parameter, for example, to use a number less than or greater than unity (e.g., locally and/or globally).

As part of a quality control process, a subset of the original database was selected as a test dataset, containing several fluid samples that were not in the training set. First each of the seven hydrocarbon "types" having their predefined compositions were utilized in flash simulations, being flashed to 4,000 psi (e.g., 28 MPa) and 212 degrees F. (e.g., 100 degrees C.) using the SRK3 EoS (a three parameter SRK based EoS). The resulting density and composition were input to a nuclear forward modeling computational framework to determine the sigma, hydrogen index and electron density of the fluid. Then the composition is predicted using the IDW technique, as described above. For each fluid tested, the 44 components were grouped into six major groups. A comparison process can be employed, for example, to determine agreement, which can validate the methodology of predicting fluid composition from the three nuclear parameters.

FIG. 14 shows an example of a graphical user interface (GUI 1410) that exhibits a comparison of the mole fraction breakdown of one of the black oil fluids tested, computed at 5,000 psi (e.g., 34 MPa) and 230 degrees F. (e.g., 110 degrees C.). Specifically, the GUI 1410 shows predicted and experimental composition data of a black oil sample. Results from another black oil reservoir sample also demonstrate the accuracy gain using the fluid types points instead of pure compounds in the IDW interpolation.

As explained, a method can include performing an inversion based on PVT compositional models and nuclear forward models to determine reservoir fluid composition. Such an approach can be implemented in a computational system for qualitative analysis and/or quantitative analysis of content of different hydrocarbon groups in fluid, while guaranteeing consistency of the various nuclear log parameters with respect to the composition of the mixture and to the reservoir pressure and temperature.

As explained, performance of different EoS and flash simulators demonstrated acceptability for three-parameter cubic equations. This increases confidence that the nuclear parameters used in the inverse distance weighting interpolation do not carry undesirable error from the density computations.

As explained, accuracy of the IDW and k-NN techniques may be degraded by the presence of noisy or irrelevant features, such as pure component points, or if the feature scales are not consistent with their physical meaning. The use of the distance to pure fluids may be detrimental in various instances because, when comparing them to a mixture, the effect of intermolecular interactions in the density of the mixture is not taken into account by both pure fluid point and mixture point. As explained, a modification to invert the distance to fluid type points provided a change of the feature space. An optimum value for number of fluid types to be considered can be part of an optimization process, which may depend on various factors, which may be selected as desired. As shown, if an IDW's power parameter is not set appropriately, the contribution of the furthest points can affect negatively the results.

As an example, a method may be applied to a wide spectrum of possible petroleum fluids. As an example, a quality control approach can include statistical analysis to determine whether there is an acceptable match between calculated mass fractions and those from compositional analyses from the laboratory. Such an approach can be utilized to validate solving the highly nonlinear problem of composition estimation. As explained, a method can include generating one or more composition logs, which may be rendered to one or more graphical user interfaces. As explained, a composition log may be for a selected interval of a trajectory of a borehole in a formation that includes fluid. For example, consider a reservoir formation (e.g., a reservoir) that includes reservoir fluid where the composition of the reservoir fluid may vary with respect to distance along an axis of the borehole. As an example, a method may include comparing a composition log to one or more other logs, which may assist in characterizing a reservoir and in performing one or more field operations with respect to the reservoir.

As an example, a 3DP technique (e.g., consider a high angle well evaluation technique as in the TECHLOG framework) can provide a workflow and computations to adjust for geometry effects on logs acquired in high angle and horizontal wells (HAHz). As an example, a layered earth model can be constructed and then an iterative (model-compare-update or automatic inversion) workflow can be utilized to deliver geometry adjusted properties which can be used in a 3DP's multi-physics inversion model. Such an inversion scheme can solve for the in-situ reservoir fluid volume, electron density, HI, and Σ, which can provide a basis to analyze quantitatively the reservoir fluid composition. Such an approach can utilize a downhole tool's nuclear measurements (e.g., ECOSCOPE tool, etc.), optionally without drawing fluid samples to the surface for analysis in a PVT lab; though such an approach may include sampling, for example, as to quality control, further analysis, etc. As an example, a method may reduce demand for sampling downhole. As an example, a downhole tool can provide a set of measurements that include contributions from rock matrix, hydrocarbon, and brine. As an example, an inversion framework for reservoir fluid properties from nuclear measurements can be implemented to obtain HI, $\rho_e$, and Σ for hydrocarbons in reservoir fluid.

Referring again to the GUI 405 of FIG. 4, such information may be utilized to generate adjusted square logs that match the layered earth model (e.g., for purposes of performing 3DP operations). As an example, a method can include estimating the mass fractions of each component of the reservoir fluid using calculated hydrocarbons HI, $\rho_e$, and Σ and the simulated response of several reservoir fluids of known composition. For example, a simulated response of a downhole tool can be performed using the SNUPAR V3C framework. Through 3D proximity in a (HI, Σ, $\rho_e$) space of a given mixture point to simulated values of the fluid types of known composition, such a method can estimate fractions of these compounds in the reservoir fluid.

As an example, the nuclear response of HI and Σ may be, in some instances relatively independent of pressure and temperature of the reservoir fluid. In some instances, large changes in a fluid's density at different pressures, however, make the computation of the volumetric and phase behavior of mixtures at reservoir pressure and temperature a desired part of a multiphysics inversion.

As an example, an EoS predicted downhole mixture density at formation pressure and temperature can be used in a workflow that includes a framework such as, for example, the SNUPAR framework, which can convert mixture composition and mixture density to nuclear parameters such as electron density index ($\rho_e$), hydrogen index (HI), and thermal neutron capture cross section (Σ).

As explained, various trials demonstrated acceptable results (see, e.g., FIG. 14). As explained, samples from more than 500 wells were provided by a laboratory where data for those samples were clustered and averaged according to their components distribution. The resulting fluids were then classified using labels for fluid types (e.g., DG, WG, GC, VO, BO, HO, SHO, ASP, etc.).

As explained, one approach can be use of pure components. However, that approach may not adequately account for intermolecular interactions in a fluid mixture such as a reservoir fluid. Thus, rather than setting up spatial distance calculations between points of pure compounds and a fluid mixture, fluid types can be utilized and, for example, an inverse distance weighting approach that can help to account for intermolecular interactions in the mixture fluid. Such an approach can be part of a workflow that solves for hydrocarbon components fractions in a reservoir fluid.

As an example, as to generating references, rather than passing the density of each pure compound at a specific pressure and temperature to the SNUPAR framework, the density of averaged fluid types computed by a PVT framework can be fed to the SNUPAR framework along with fluid types' composition (e.g., as known). Such an approach can simulate a number of nuclear parameter values, which can include HI, $\Sigma$, and $\rho_e$ (e.g., as determined using the substances' chemical formula, density, and nuclear source type as input).

As mentioned, nuclear parameter measurements can include contributions from rock matrix, hydrocarbon, and brine. An inversion framework may be implemented that allows for obtaining reservoir fluid properties, such as HI, $\rho_e$, and $\Sigma$. For example, consider use of the TECHLOG 3DP inversion framework. The simulated HI, $\Sigma$, and $\rho_e$ from fluid types can then be compared against these inverted reservoir fluid values.

As an example, for qualitative and quantitative estimates of individual component fractions, a method can include using Euclidean distances in 3D space (HI and $\Sigma$ vs. $\rho_e$). For example, consider first calculating 2-norm of the distance vector from the mixture data point to each fluid type. In such an approach, the 2-norm can be Euclidean length, defined in the 3-dimensional Euclidean space. As an example, a method can include normalizing individual distances to fluid types and inverting the normalized distances to fluid types. Such an approach acts to make the shortest distance of greatest importance and give it the highest fraction value. Such an approach can include multiplying by the components mass fractions of each fluid type and then summing the contribution from each fluid type to output the mass fraction of each component in the fluid mixture. As an example, values may be normalized to handle truncation error.

To assess the approach, after calculating compositions of multiple mixtures, results using distances to pure compounds and using distances to fluid types were compared against experimental data. The comparison demonstrated an improvement over the pure component approach, for example, assessment of a black oil sample using the pure component approach showed erroneous peaks in the concentration of C16, C17 and C18 alkanes, while also missing the light alkanes and C30+ fraction response. As to specifics of the particular fluid types approach, 44 components were grouped into fluid types.

Figure 15:
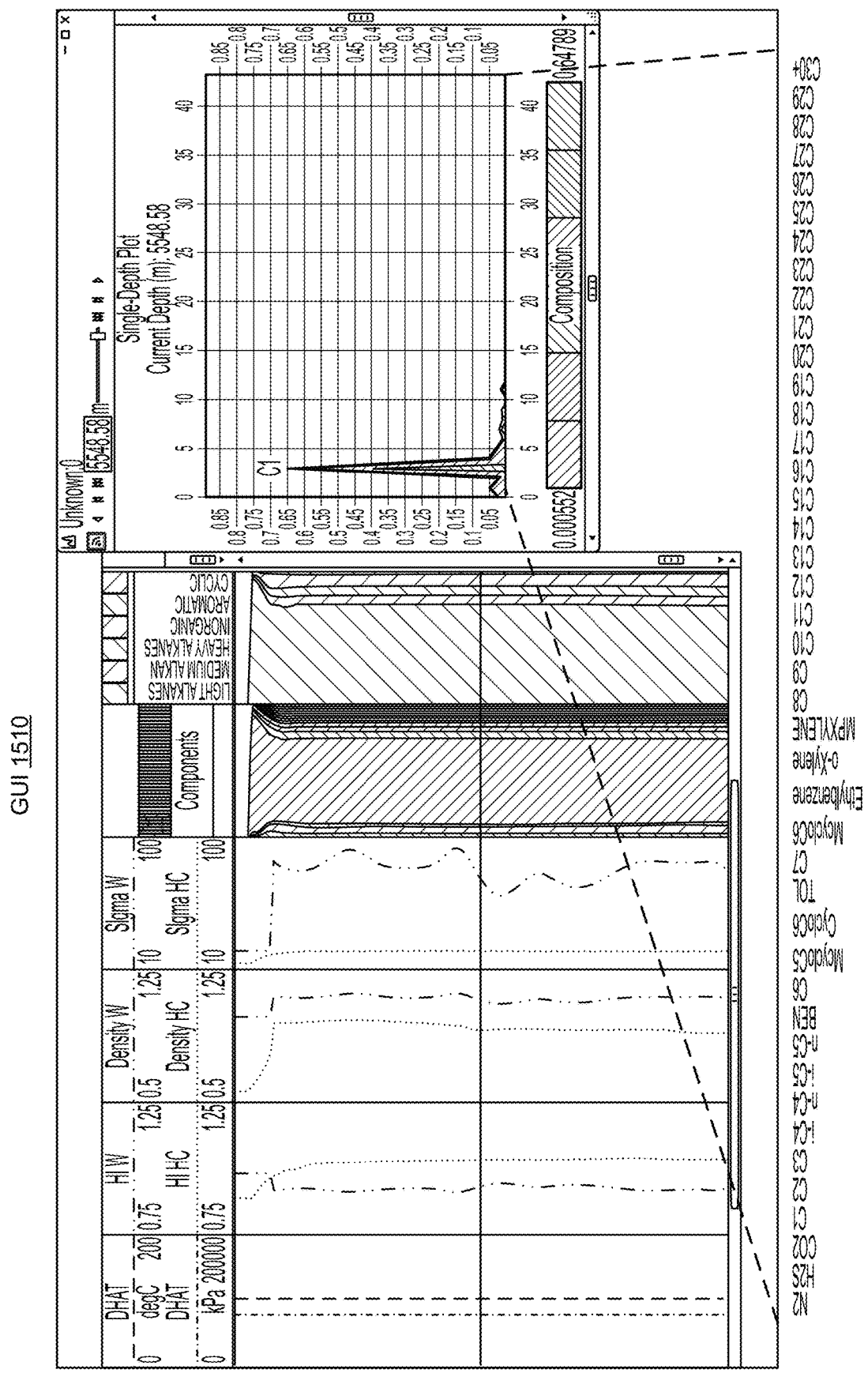
FIG. 15 illustrates an example of a graphical user interface.

FIG. 15 shows an example of a graphical user interface (GUI) 1510 that includes various logs, including a composition log. The GUI 1510 shows solved fluid nuclear properties and composition as estimated. The logs are references with respect to a distance metric and show temperature and pressure, hydrogen index (water and hydrocarbon), electron density (water and hydrocarbon), sigma (water and hydrocarbon), components, fluid types (e.g., light alkanes, medium alkanes, heavy alkanes, inorganic, aromatic, cyclic, and at a selected distance metric (e.g., depth), a graphic of fraction versus type of component (e.g., according to number of carbons, arrangement of carbons, etc.). In the example, a peak is shown with a fraction of approximately 0.65, which can be coded (e.g., color, hatched, etc.) to correspond to a fluid type (e.g., light alkanes, etc.). As shown, the GUI 1510 can include a slider graphic control that can receive input to navigate the distance metric (e.g., measured depth, etc.).

Figure 16:
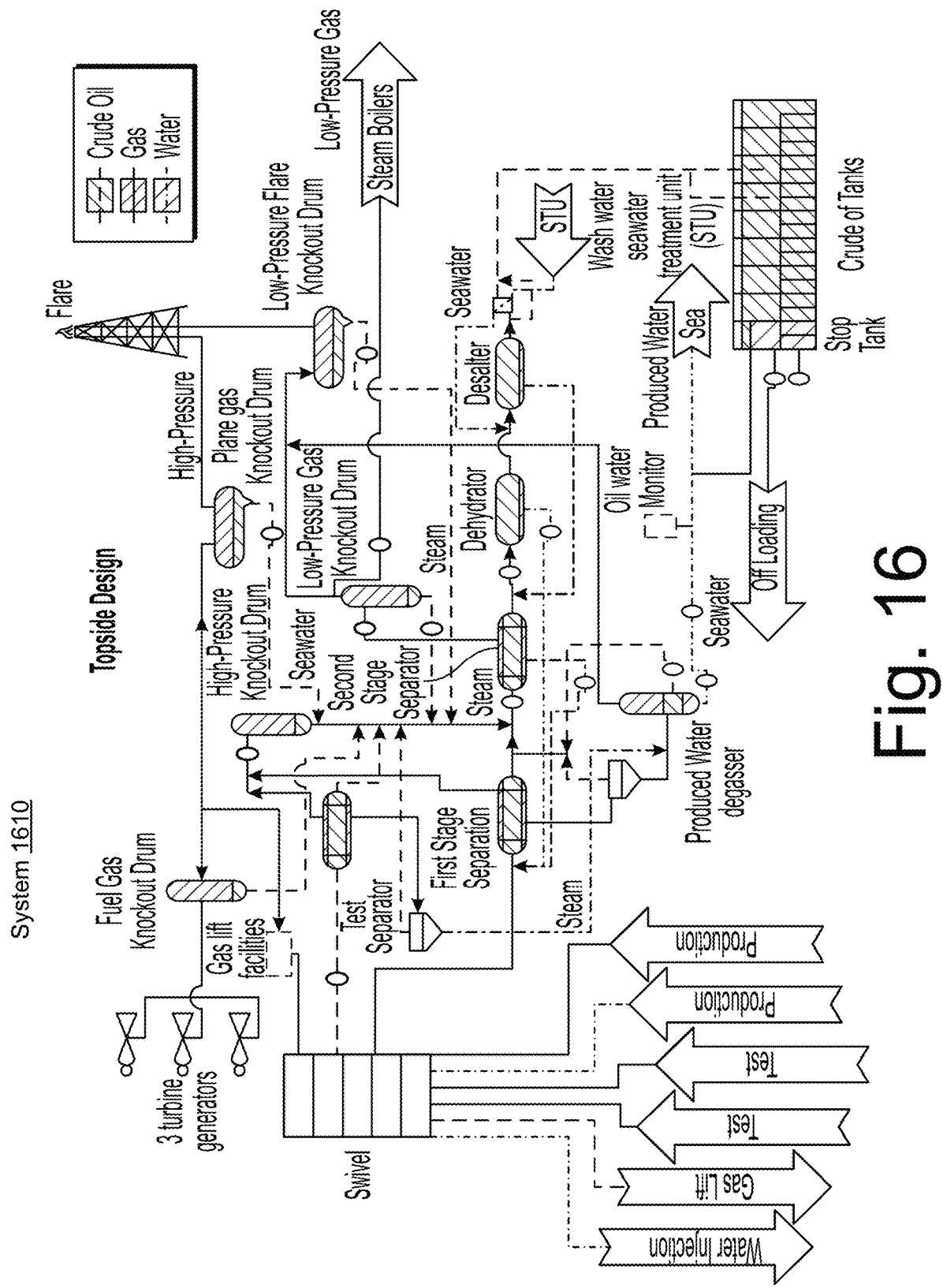
FIG. 16 illustrates an example of a system.

FIG. 16 shows an example of a system 1610. As an example, such a system may be utilized in a field as part of one or more operations. As shown, operations with respect to a formation can include water injection, gas lift, testing, and production. As an example, a workflow can include utilizing one or more types of equipment in combination with a computational framework to estimate composition of one or more types of fluids that may be in a formation or formations; or, for example, in one or more pieces of surface equipment (e.g., in a pipeline, in a separator, in a flare, etc.). As an example, the system 1610 can include one or more controllers that can be controlled using composition as estimated according to a method or methods (e.g., workflow or workflows) as described herein. As an example, a method can include comparing surface composition and downhole composition of one or more fluids, which may be, for example, utilized to adjust a computational framework (e.g., optimization, quality control, etc.).

As to various tools, as mentioned, a workflow may include emission of neutrons by a pulsed neutron generator (PNG) of a tool to induce emission of gamma rays from a formation via interactions such as inelastic scattering interactions and thermal neutron capture interactions, which can produce gamma rays with a specific set of characteristic energies. In turn, gamma rays may be detected by a $LaBr_3$:Ce scintillator coupled to a high-temperature spectroscopy photomultiplier, producing signals that can be integrated, digitized, and processed by a high-performance pulse-height analyzer. Such an analyzer may determine, for example, pulse height (proportional to energy) of individually detected gamma rays and accumulate pulse-height histograms (spectra) that tally counts versus pulse height. Spectra may be acquired, for example, during and after each neutron burst, which helps to enable separation of inelastic and capture gamma rays. As an example, an individual spectrum may be decomposed into a linear combination of standard spectra from individual elements, which can involve adjustment for one or more environmental and/or electronic factors. As an example, coefficients of linear combination of standard spectra may be converted to elemental weight fractions, for example, via a modified geochemical oxides closure model, an inversion approach, etc. As to interpretation, various approaches may be implemented to generate mineralogy and lithologic fractions from the elemental concentration logs. As an example, a sequential SpectroLith processing approach may be used, which is based on the derivation of empirical relationships between elemental concentrations and mineral concentrations. As example, an iterative inversion technique may be implemented (e.g., consider the TECHLOG QUANTI multicomponent inversion ELAN module).

Various methods described herein may be implemented using various computer-readable media (CRM) blocks (e.g., non-transitory media that are not carrier waves and that are not signals). Such blocks generally include instructions suitable for execution by one or more processors (or cores) to instruct a computing device or system to perform one or more actions. As an example, a single medium may be configured with instructions to allow for, at least in part, performance of various actions of a method. As an example, a computer-readable storage medium (CRM) is a non-transitory computer-readable storage medium that is not a carrier wave and that is not a signal. One or more CRM blocks may be provided for graphical user interfaces (GUIs), etc. One or more CRM blocks may be provided for rendering information to a display, etc. (e.g., consider rendering a model to a display, etc.).

Figure 17:
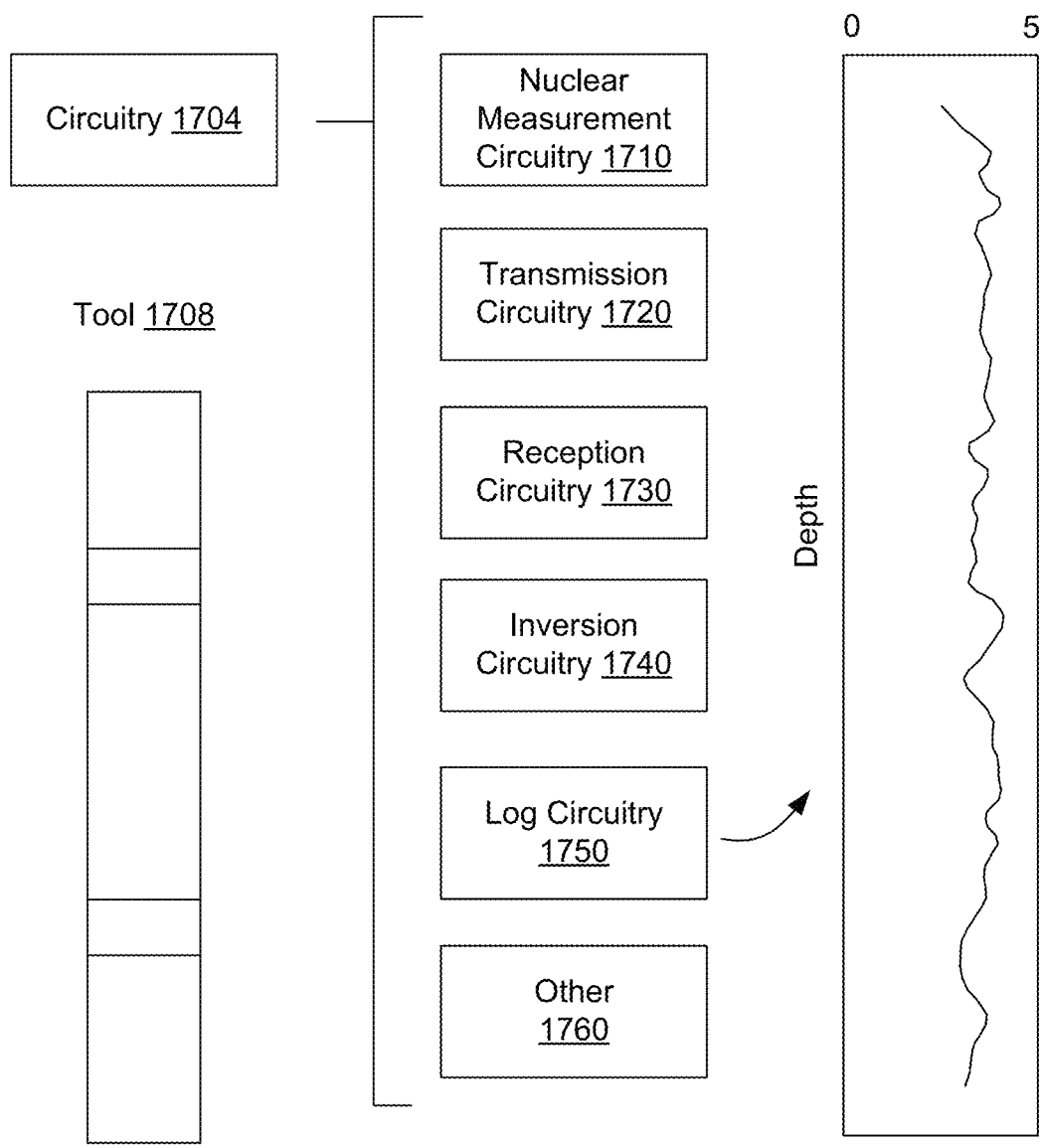
FIG. 17 illustrates an example of a system and an example of a log.

FIG. 17 shows an example of a tool system 1700 as a formation characterization system that includes circuitry 1704 and a tool 1708 where one or more portions of the circuitry 1704 may be disposed within the tool 1708 and/or otherwise operatively coupled to the tool 1708 to receive data that are measurements and/or other data therefrom. The tool 1708 can include features of a tool or tools as in, for example, FIG. 3, FIG. 5, etc. As shown, the circuitry 1704 can include nuclear measurements circuitry 1710, transmission circuitry 1720, reception circuitry 1730, inversion circuitry 1740, log circuitry 1750 and one or more other components 1760. As shown, the log circuitry 1750 can provide a log such as the log 1754 (see, e.g., logs of FIG. 4, etc.). As an example, the log circuitry 1750 can output a composition log for fluid in a portion of a formation traversed by the tool 1708 (e.g., a portion of a borehole).

Figure 18:
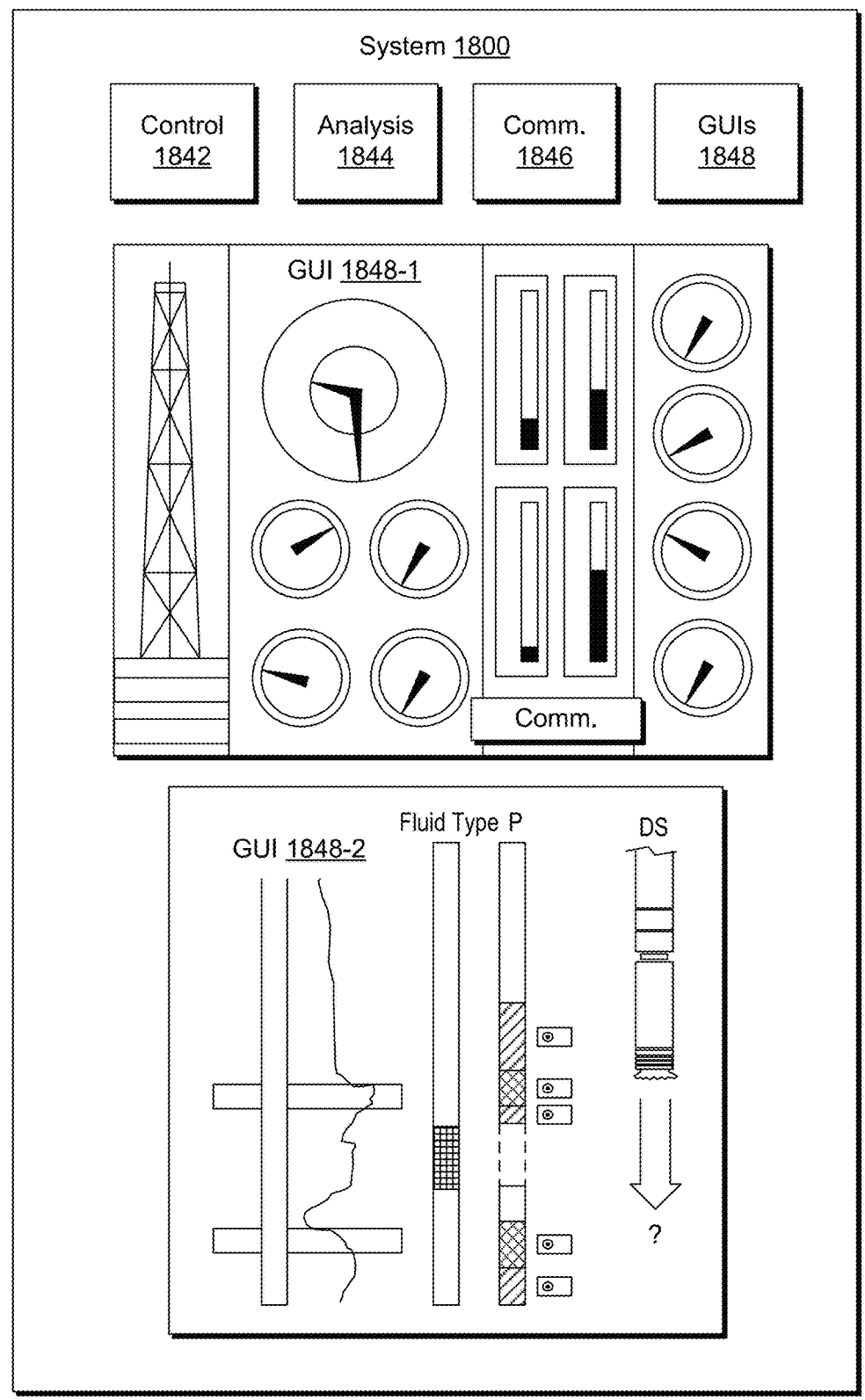
FIG. 18 illustrates an example of a system.

FIG. 18 shows an example of a system 1800 that includes various components such as a control component 1842, an analysis component 1844, a communication component 1846 and one or more graphical user interface components 1848. As an example, the system 1800 may include one or more features of a framework such as, for example, the TECHLOG framework, the INTERACT framework, etc. As an example, a GUI 1848-1 may render information as to real-time conditions at a site (e.g., a well site) and a GUI 1848-2 may render information as to one or more regions within an environment. For example, a region may be a drilled region, a region to be drilled, etc. As shown in the GUI 1848-2, values may be rendered with respect to a spatial dimension such as depth (e.g., measured depth, true vertical depth, etc.). Such values may indicate composition of fluid in a region. In such an example, equipment may be controlled to account for one or more operations for the region. As mentioned, a region may be subjected to fracturing via hydraulic fluid that is introduced to a borehole to contact the region and generate one or more fractures. Such fluid can be tailored to the region based at least in part on one or more fluid composition values, which may be associated with a portion of a reservoir and characterize that portion of the reservoir. For example, consider a relationship between maturity and wettability or hydrophilicity/hydrophobicity where a surfactant or surfactants may be selected for inclusion in the fluid (e.g., type, concentration, etc.).

As an example, various values may indicate lithology of a region, for example, consider a kerogen deposit. As an example, the GUI 1848-2 may include one or more of a fluid type graphic, an operational parameter(s) graphic (P) and a drill string (DS) graphic. In such an example, equipment (e.g., drillstring equipment) may be controlled to account for drilling into a formation, etc.

As an example, a geologic environment may be an environment that includes a reservoir or reservoirs. As an example, a geologic environment may be an environment that is a geothermal environment. As an example, a geologic environment may be an environment that is utilized for storage of waste such as, for example, nuclear waste. As an example, a geologic environment may be a non-oil and gas environment (e.g., as may be suitable for production). As an example, a geologic environment may be a hydrologic environment.

As an example, a method can include receiving measurements of a fluid mixture where the measurements are acquired by at least one downhole tool; performing a multiphysics inversion of the measurements to generate nuclear parameter values for the fluid mixture; performing a multivariate interpolation using the generated nuclear parameter values that accounts for intermolecular interactions in the fluid mixture; and determining a composition of the fluid mixture based on the multivariate interpolation. In such an example, the nuclear parameter values can include at least two of electron density, hydrogen index and sigma. As an example, the nuclear parameter values can include at least electron density.

As an example, a multivariate interpolation can be in a multi-nuclear parameter space where points are provided that are defined by nuclear parameter values for a pre-defined number of fluid types. As an example, such points may be considered to be reference points (e.g., a reference point for each of the pre-defined number of fluid types). As an example, a multi-nuclear parameter space can be defined using at least two of electron density, hydrogen index and sigma.

As an example, a multivariate interpolation can include inverse distance weighting (IDW). Such a technique can account for intermolecular interactions. As an example, an IDW technique can include a power parameter that may be adjustable. For example, a system can render a graphical user interface to a display with a control for a power parameter that allows for receipt of input to adjust the power parameter and perform the IDW technique. As an example, such a system can include a GUI for selecting a number of different fluid types, which may be selected from a pre-defined set of different fluid types (see, e.g., the method 700 of FIG. 7).

As an example, a multivariate interpolation can include using points for a plurality of different fluid types defined in a multi-nuclear parameter space where at least one of the fluid types is a mixture of components where the components include hydrocarbons. In such an example, the points for a plurality of different fluid types can be defined by nuclear parameter values determined using forward modeling of density data generated for fluid types of known compositions. In such an example, the density data can be generated using a flash simulator at a specified pressure and temperature (e.g., or pressures and temperatures). As an example, a database or databases can include values as output by a framework such as, for example, the SNUPAR framework (e.g., a forward modeling framework that receives density values of fluid types as may be output by a flash simulator). As an example, a specified pressure and temperature (e.g., a duple) can correspond to a pressure and a temperature of fluid mixture measurements as acquired by at least one downhole tool. As an example, a downhole tool or tools may acquire a series of measurements along a length of a borehole where such measurements can include pressure and temperature and measurements sufficient to perform a 3DP inversion to generate nuclear parameter values of reservoir fluid (e.g., a fluid mixture) at a number of positions along the length of the borehole. As mentioned, an analysis can generate a composition log that includes a depth metric that can be a measured depth along a length of a borehole. As explained, measurements can correspond to a measured depth along a borehole trajectory.

As an example, a method can include rendering a graphical representation of a composition of a fluid mixture to a display. Such a graphical representation may be in the form of a plot in a multi-dimensional nuclear parameter space, in the form of a log, in the form of a plot (e.g., fraction versus molecular characteristics), etc.

As an example, a method can include receiving a depth metric via a graphical user interface and, in response, rendering a composition plot for the fluid mixture that corresponds to the depth metric. In such an example, the composition plot can be derived at least in part from a spatial distance analysis of measurement-derived nuclear parameter values and nuclear parameter values from forward modeling with respect to pre-defined fluid types (e.g., at particular temperature(s) and pressure(s)).

As an example, a method can include determining the composition of a fluid mixture for a position of a downhole tool and, responsive to moving the downhole tool to a different position, determining the composition of the fluid mixture at the different position. For example, as explained with respect to FIG. 7, the block 738 may be provided in the form of a database or databases such that flash simulation is performed in advance. Such an approach can expedite the processing of real-time measurements, for example, to generate a real-time composition log.

As an example, where a downhole tool includes features for fluid sampling, a method can include positioning the downhole tool for fluid sampling using composition output (e.g., a composition log) and acquiring a fluid sample. In such an approach, the fluid sample may be analyzed downhole and/or may be brought to surface for analysis at a site and/or at a lab. Such an approach may optionally be utilized to quality control composition output (e.g., a composition log).

As an example, a method can include adjusting a drilling operation using an output composition of a fluid mixture. For example, consider a downhole tool that is part of a drill string where the downhole tool can acquire measurements that can be processed using a 3DP inversion process to generate nuclear parameter values for reservoir fluid. In such an example, a spatial distance analysis may be performed to assess the reservoir fluid with respect to pre-determined fluid types such that composition output can be generated for the reservoir fluid. In such an example, the drilling operation may be adjusted to stay within bounds of a reservoir that includes the reservoir fluid (e.g., a pay zone, etc.). Such an approach may optionally be implemented during drilling, for example, to steer a drill bit with respect to a reservoir.

As an example, a composition may be output in one or more forms. For example, consider a mass fraction composition or a mole fraction composition; noting that other forms may be utilized.

As an example, a method can include outputting forward modeling nuclear parameter values of fluids of known compositions using one or more pre-defined fluid types where a composition of a fluid mixture can be determined using at least some of the pre-defined fluid types. Such a method can include defining the pre-defined fluid types by clustering utilizing a k value that indicates a number of clusters and corresponding number of pre-defined fluid types.

As an example, a method can include performing a multivariate interpolation technique using a computational framework that includes at least one processor.

As an example, a system can include a processor; memory accessibly by the processor; instructions stored in the memory and executable by the processor to instruct the system to: receive measurements of a fluid mixture where the measurements are acquired by at least one downhole tool; perform a multiphysics inversion of the measurements to generate nuclear parameter values for the fluid mixture; perform a multivariate interpolation using the generated nuclear parameter values that accounts for intermolecular interactions in the fluid mixture; and determine a composition of the fluid mixture based on the multivariate interpolation. Such a system may be utilized to perform various methods.

As an example, one or more computer-readable storage media can include processor-executable instructions where the processor-executable instructions include instructions to instruct a computer to: receive measurements of a fluid mixture where the measurements are acquired by at least one downhole tool; perform a multiphysics inversion of the measurements to generate nuclear parameter values for the fluid mixture; perform a multivariate interpolation using the generated nuclear parameter values that accounts for intermolecular interactions in the fluid mixture; and determine a composition of the fluid mixture based on the multivariate interpolation.

Figure 19:
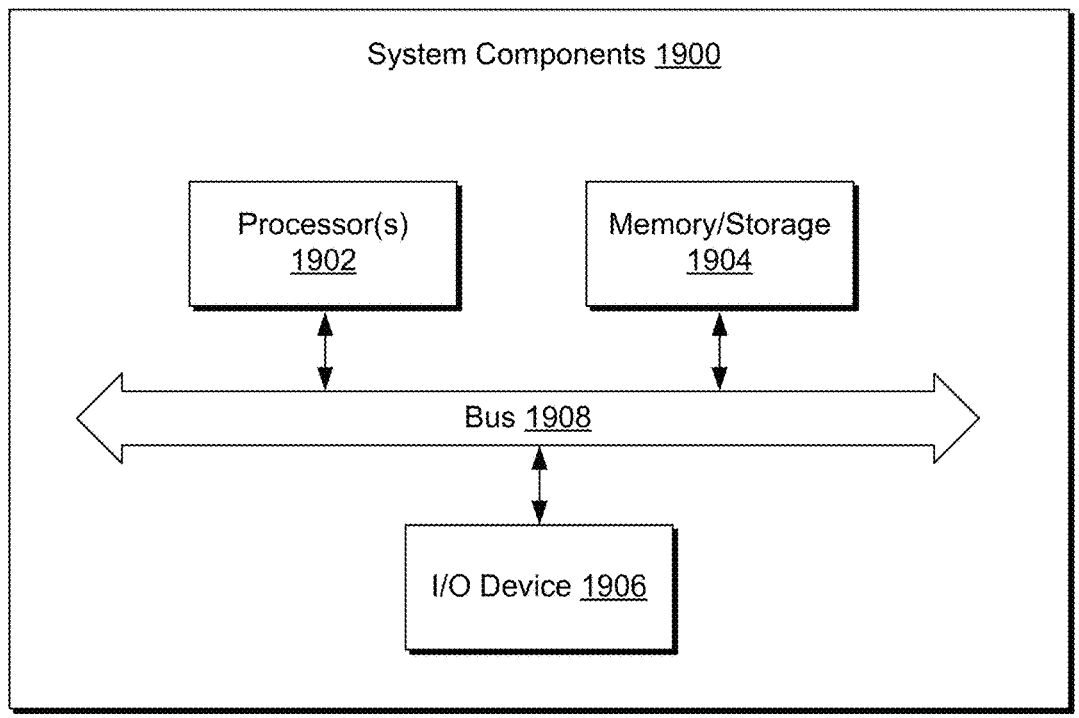
FIG. 19 illustrates example components of a system and a networked system.
Figure 19:
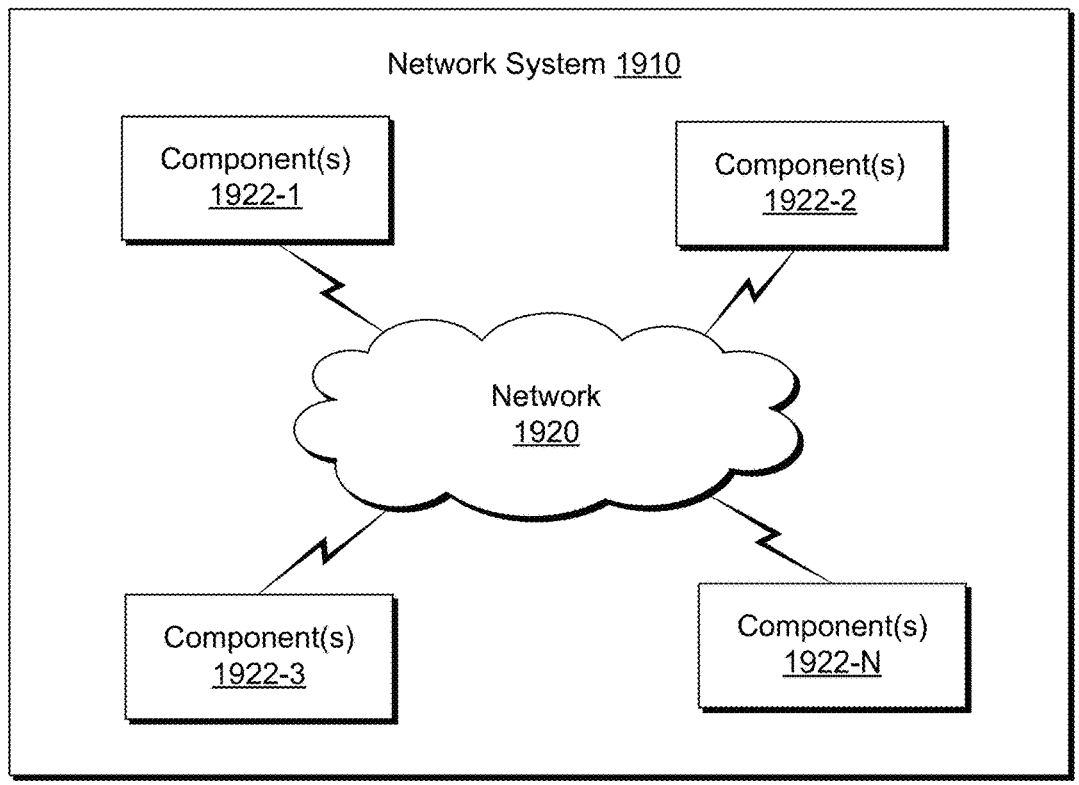

FIG. 19 shows components of an example of a computing system 1900 and an example of a networked system 1910. A system such as the system 1700 of FIG. 17, the system 560 of FIG. 5, etc., may include one or more of the features of the system 1900 and/or the system 1910. The system 1900 includes one or more processors 1902, memory and/or storage components 1904, one or more input and/or output devices 1906 and a bus 1908. In an example embodiment, instructions may be stored in one or more computer-readable media (e.g., memory/storage components 1904). Such instructions may be read by one or more processors (e.g., the processor(s) 1902) via a communication bus (e.g., the bus 1908), which may be wired or wireless. The one or more processors may execute such instructions to implement (wholly or in part) one or more attributes (e.g., as part of a method). A user may view output from and interact with a process via an I/O device (e.g., the device 1906). In an example embodiment, a computer-readable medium may be a storage component such as a physical memory storage device, for example, a chip, a chip on a package, a memory card, etc. (e.g., a computer-readable storage medium).

In an example embodiment, components may be distributed, such as in the network system 1910. The network system 1910 includes components 1922-1, 1922-2, 1922-3, . . . 1922-N. For example, the components 1922-1 may include the processor(s) 1902 while the component(s) 1922-3 may include memory accessible by the processor(s) 1902. Further, the component(s) 1902-2 may include an I/O device for display and optionally interaction with a method. The network may be or include the Internet, an intranet, a cellular network, a satellite network, etc.

As an example, a device may be a mobile device that includes one or more network interfaces for communication of information. For example, a mobile device may include a wireless network interface (e.g., operable via IEEE 802.11, ETSI GSM, BLUETOOTH, satellite, etc.). As an example, a mobile device may include components such as a main processor, memory, a display, display graphics circuitry (e.g., optionally including touch and gesture circuitry), a SIM slot, audio/video circuitry, motion processing circuitry (e.g., accelerometer, gyroscope), wireless LAN circuitry, smart card circuitry, transmitter circuitry, GPS circuitry, and a battery. As an example, a mobile device may be configured as a cell phone, a tablet, etc. As an example, a method may be implemented (e.g., wholly or in part) using a mobile device. As an example, a system may include one or more mobile devices.

As an example, a system may be a distributed environment, for example, a so-called "cloud" environment where various devices, components, etc. interact for purposes of data storage, communications, computing, etc. As an example, a device or a system may include one or more components for communication of information via one or more of the Internet (e.g., where communication occurs via one or more Internet protocols), a cellular network, a satellite network, etc. As an example, a method may be implemented in a distributed environment (e.g., wholly or in part as a cloud-based service). As an example, a framework such as the TECHLOG framework for petrophysics may be implemented at least in part in a cloud environment. For example, the tool system 1700 of FIG. 17 may be operatively coupled to cloud resources (e.g., network equipment, compute equipment, memory devices, etc.).

As an example, a mobile device may be configured with a browser or other application (e.g., app, etc.) that can operatively couple to cloud resources and, for example, optionally to local resources (e.g., equipment at a rig site, wireline site, etc.). For example, a system can include performing computations locally and/or remotely where rendering of a log or logs may occur locally and/or remotely. Remote rendering may be to a mobile device where, for example, a user can see, optionally in real time, maturity values for a formation or formations, which may be from induction measurements acquired in one or more boreholes and processed by a system such as a system that includes one or more features of the tool system 1700 of FIG. 17, the system 560 of FIG. 5, etc.

As an example, information may be input from a display (e.g., consider a touchscreen), output to a display or both. As an example, information may be output to a projector, a laser device, a printer, etc. such that the information may be viewed. As an example, information may be output stereographically or holographically. As to a printer, consider a 2D or a 3D printer. As an example, a 3D printer may include one or more substances that can be output to construct a 3D object. For example, data may be provided to a 3D printer to construct a 3D representation of a subterranean formation. As an example, layers may be constructed in 3D (e.g., horizons, etc.), geobodies constructed in 3D, etc. As an example, holes, fractures, etc., may be constructed in 3D (e.g., as positive structures, as negative structures, etc.).

Although only a few example embodiments have been described in detail above, those skilled in the art will readily appreciate that many modifications are possible in the example embodiments. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words "means for" together with an associated function.

What is claimed is:

1. A method comprising:
   receiving measurements of a fluid mixture wherein the measurements are acquired by at least one downhole tool;
   performing a multiphysics inversion of the measurements to generate nuclear parameter values for the fluid mixture, wherein the nuclear parameter values comprise electron density and density of hydrogen relative to that of water, electron density and thermal neutron capture cross section or electron density, density of hydrogen relative to that of water and thermal neutron capture cross section;
   performing a multivariate interpolation using the generated nuclear parameter values that accounts for intermolecular interactions in the fluid mixture, wherein the multivariate interpolation comprises using points for a plurality of different fluid types defined in a multi-nuclear parameter space wherein each of the fluid types is a mixture of components wherein the components comprise hydrocarbons; and
   determining a composition of the fluid mixture based on the multivariate interpolation.

2. The method of claim 1 wherein the multivariate interpolation comprises inverse distance weighting.

3. The method of claim 2 wherein the inverse distance weighting accounts for intermolecular interactions.

4. The method of claim 1 wherein the points for a plurality of different fluid types are defined by nuclear parameter values determined using forward modeling of density data generated for fluid types of known compositions.

5. The method of claim 4 wherein the density data are generated using a flash simulator at a specified pressure and temperature.

6. The method of claim 5 wherein the specified pressure and temperature correspond to a pressure and a temperature of the fluid mixture measurements as acquired by at least one downhole tool.

7. The method of claim 1 wherein the measurements correspond to a measured depth along a borehole trajectory.

8. The method of claim 1 comprising rendering a graphical representation of the composition of the fluid mixture to a display.

9. The method of claim 1 comprising receiving a depth metric via a graphical user interface and, in response, rendering a composition plot for the fluid mixture that corresponds to the depth metric.

10. The method of claim 1 comprising determining the composition of the fluid mixture for a position of the downhole tool and, responsive to moving the downhole tool to a different position, determining the composition of the fluid mixture at the different position.

11. The method of claim 1 comprising adjusting a drilling operation using the composition of the fluid mixture.

12. The method of claim 1 wherein the composition comprises a mass fraction composition or a mole fraction composition.

13. The method of claim 1 comprising outputting forward modeling nuclear parameter values of fluids of known compositions using one or more pre-defined fluid types wherein the composition of the fluid mixture comprises at least some of the pre-defined fluid types.

14. The method of claim 13 comprising defining the pre-defined fluid types by clustering utilizing a k value that indicates a number of clusters and corresponding number of pre-defined fluid types.

15. The method of claim 1 wherein the multivariate interpolation is performed using a computational framework that comprises at least one processor.

16. A system comprising:
   a processor;
   memory accessibly by the processor; and
   instructions stored in the memory and executable by the processor to instruct the system to:
     receive measurements of a fluid mixture wherein the measurements are acquired by at least one downhole tool;
     perform a multiphysics inversion of the measurements to generate nuclear parameter values for the fluid mixture, wherein the nuclear parameter values comprise electron density and density of hydrogen relative to that of water, electron density and thermal neutron capture cross section or electron density, density of hydrogen relative to that of water and thermal neutron capture cross section;

perform a multivariate interpolation using the generated nuclear parameter values that accounts for intermolecular interactions in the fluid mixture, wherein the multivariate interpolation comprises using points for a plurality of different fluid types defined in a multi-nuclear parameter space wherein each of the fluid types is a mixture of components wherein the components comprise hydrocarbons; and determine a composition of the fluid mixture based on the multivariate interpolation.

17. One or more computer-readable storage media comprising processor-executable instructions wherein the processor-executable instructions comprise instructions to instruct a computer to:

receive measurements of a fluid mixture wherein the measurements are acquired by at least one downhole tool;

perform a multiphysics inversion of the measurements to generate nuclear parameter values for the fluid mixture, wherein the nuclear parameter values comprise electron density and density of hydrogen relative to that of water, electron density and thermal neutron capture cross section or electron density, density of hydrogen relative to that of water and thermal neutron capture cross section;

perform a multivariate interpolation using the generated nuclear parameter values that accounts for intermolecular interactions in the fluid mixture, wherein the multivariate interpolation comprises using points for a plurality of different fluid types defined in a multi-nuclear parameter space wherein each of the fluid types is a mixture of components wherein the components comprise hydrocarbons; and determine a composition of the fluid mixture based on the multivariate interpolation.

\* \* \* \* \*